US007271198B2

(12) United States Patent
Kammer et al.

(10) Patent No.: US 7,271,198 B2
(45) Date of Patent: Sep. 18, 2007

(54) METHOD OF TREATING AUTOIMMUNE DISEASES

(75) Inventors: Gary M. Kammer, Lewisville, NC (US); Nilamadhab Mishra, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 322 days.

(21) Appl. No.: 10/151,481

(22) Filed: May 20, 2002

(65) Prior Publication Data

US 2003/0114525 A1 Jun. 19, 2003

Related U.S. Application Data

(63) Continuation of application No. PCT/US01/43871, filed on Nov. 19, 2001, and a continuation-in-part of application No. 09/718,195, filed on Nov. 20, 2000, now abandoned.

(51) Int. Cl.
*A61K 31/136* (2006.01)
*C12Q 1/44* (2006.01)
*C12N 9/18* (2006.01)

(52) U.S. Cl. ......................... 514/645; 435/19; 435/197

(58) Field of Classification Search .................. 435/19, 435/197; 530/2; 514/645

See application file for complete search history.

(56) References Cited

U.S. PATENT DOCUMENTS

| | | | | |
|---|---|---|---|---|
| 4,690,918 | A | 9/1987 | Beppu et al. | |
| 5,843,885 | A | 12/1998 | Benedict et al. | |
| 5,939,455 | A | 8/1999 | Rephaeli | |
| 5,993,845 | A | 11/1999 | Geerts et al. | |
| 6,071,923 | A | 6/2000 | Nudelman et al. | |
| 6,124,495 | A | 9/2000 | Neiss et al. | |
| 6,211,440 | B1 | 4/2001 | Briggs et al. | |
| 6,323,334 | B1 | 11/2001 | Kingsbury et al. | |
| 6,403,555 | B1 | 6/2002 | Skov | |
| 6,544,957 | B2 | 4/2003 | Kern et al. | |
| 6,667,341 | B2 * | 12/2003 | Lan-Hargest et al. | 514/547 |
| 6,855,515 | B1 | 2/2005 | Rosen et al. | |
| 2003/0082666 | A1 | 7/2004 | Kammer et al. | |
| 2006/0030626 | A1 | 2/2006 | Kammer et al. | |

FOREIGN PATENT DOCUMENTS

| | | | |
|---|---|---|---|
| GB | 2 309 696 | A | 8/1997 |
| JP | 07206670 | A * | 8/1995 |
| WO | WO93/19778 | A1 | 10/1993 |
| WO | WO97/11366 | | 3/1997 |
| WO | WO 97/35990 | | 10/1997 |
| WO | WO97/47307 | | 12/1997 |
| WO | WO98/48825 | | 11/1998 |
| WO | WO99/37150 | | 7/1999 |
| WO | WO 00/08048 | | 2/2000 |
| WO | WO00/21979 | A2 * | 4/2000 |
| WO | WO 00/21979 | A2 | 4/2000 |
| WO | WO 00/23567 | | 4/2000 |

OTHER PUBLICATIONS

English Machine Translation of JP 07206670 from JAPIO website.*

Taber's Medical Dictionary, 15th edition. 1981 (F.A. Davis Company: Philadelphia, PA) p. 982.*

Kohge et al. "Promotion of antigen-specific antibody production in murine B cells by a moderate increase in histone acetylation" Biochem. Pharmacol. (1998) 56: 1359-1364.*

Andrews et al., *Anti-malarial effect of histone deacetylation inhibitors and mammalian tumour cytodifferentiating agents*, International Journal of Parasitology, vol. 30, 2000, pp. 761-768.

Barnes, *Anti-inflammatory actions of glucocorticoids: molecular mechanisms*, Clinical Science, vol. 94, 1998, pp. 557-572.

Berden et al., *Role of Nucleosomes for Induction and Glomerular Binding of Autoantibodies in Lupus Nephritis*, Current Opinion in Nephrology and Hypertension, vol. 8, No. 3, May 1999, pp. 299-306.

Brey et al., *Anti-Intercellular Adhesion Molecule-1 (ICAM-1) antibody treatment prevents central and peripheral nervous system disease in autoimmune-prone mice*, Lupus, vol. 6, 1997, pp. 645-651.

Brosch et al., *Abstract, Inhibition of maize histone deacetylases by HC toxin, the host-selective toxin of Cochliobolus carbonum*, The Plant Cell, vol. 7, 1995, pp. 1941-1950.

Chiurazzi et al., *Synergistic Effect of Histone Hyperacetylation and DNA demethylation in the reactivation of the FMR1 gene*, Human Molecular Genetics, vol. 8, No. 12, 1999, pp. 2317-2323.

Cress et al., *Histone Deacetylases, Transcriptional Control, and Cancer*, Journal of Cellular Physiology, vol. 184, 2000, pp. 1-16.

Dangond et al., *Differential Display Cloning of a Novel Human Histone Deacetylase (HDAC3) cDNA from PHA-Activated Immune Cells*, Biochemical and Biophysical Research Communications, vol. 242, 1998, pp. 648-652.

Darkin-Rattray et al., *Apicidin: A novel antiprotozoal agent that inhibits parasite histone deacetylase*, Proc. Natl. Acad. Sci., USA, vol. 93, Nov. 1996, pp. 13143-13147.

Dayal et al., *The T Cell Enigma in Lupus*, Arthritis & Rheumatism, vol. 39, No. 1, Jan. 1, 1996, pp. 23-33.

Desai-Mehta et al., *Hyperexpression of CD40 Ligand by B and T Cells in Human Lupus and Its Role in Pathogenic Autoantibody Production*, J. Clin. Invest., vol. 97, No. 9, May 1996, pp. 2063-2073.

Finnin et al., *Structures of a histone deacetylase homologue bound to the TSA and SAHA inhibitors*, Nature, vol. 401, Sep. 9, 1999, pp. 188-193.

(Continued)

*Primary Examiner*—Leon B. Lankford, Jr.
*Assistant Examiner*—Susan Hanley
(74) *Attorney, Agent, or Firm*—Myers Bigel Sibley & Sajovec, P.A.

(57) ABSTRACT

A method of treating an autoimmune disease comprising administering to the subject a treatment effective amount of a histone hyperacetylating agent, or a pharmaceutically acceptable salt thereof.

6 Claims, 25 Drawing Sheets

OTHER PUBLICATIONS

Glick et al., *PubMed Abstract, Hybrid polar histone deacetylase inhibitor induces apoptosis and CD95/CD95 Ligand expression in human neuroblastoma*, Cancer Res, vol. 59, No. 17, Sep. 1, 1999, pp. 4392-4399.

Guan et al., *PubMed Abstract. Drg-1 as a differentiation-related, putative metastatic suppressor gene in human colon cancer*, Cancer Res, vol. 60, No. 3, Feb. 1, 2000, pp. 749-755.

Horwitz et al., *T Lymphocytes, Natural Killer Cells, Cytokines, and Immune Regulation*, Dubois' Lupus Erythematosus, Wallace et al., eds., (Williams & Wilkins, Baltimore, 1997), pp. 155-194.

Huang et al., *Inhibition of IL-8 Gene Expression in CACO-2 Cells by Compounds Which Induce Histone Hyperacetylation*, Cytokine, vol. 9, No. 1 Jan. 1997, pp. 27-36.

Huggins et al., *Antibodies from systemic lupus erythematosus (SLE) sera define differential release of autoantigens from cell lines undergoing apoptosis*, Clin Exp Immunol, vol. 118, 1999, pp. 322-328.

Kijima et al., *Trapoxin, an Antitumor Cyclic Tetrapeptide, is an Irreversible Inhibitor of Mammalian Histone Deacetylase*, The Journal of Biological Chemistry, vol. 268, No. 30, Oct. 25, 1993, pp. 22429-22435.

Kim et al., *Ikaros DNA-Binding Proteins Direct Formation of Chromatin Remodeling Complexes in Lymphocytes*, Immunity, vol. 10, Mar. 1999, pp. 345-355.

Kim et al., *PubMed Abstract, Oxamflatin is a novel antitumor compound that inhibits mammalian histone deacetylase*, Oncogene, vol. 18, No. 15, Apr. 15, 1999, pp. 2461-1470.

Kimberley, *Characteristics of Immune Complexes and Principles of Immune Complex Diseases*, Chapter 27, Arthritis and Allied Conditions: A Textbook of Rheumatology, W. J. Koopman, Ed., (williams & Wilkins, Baltimore, 1997), pp. 529-543.

Kohge et al., *PubMed Abstract, Promotion of antigen-specific antibody production in murine B cells by a moderate increase in histone acetylation*, Biochem Pharmacol, vol. 56, No. 10, Nov. 15, 1998, pp. 1359-1364.

Koipally et al., *Repression by Ikaros and Aiolos is mediated through histone deacetylase complexes*, The EMBO Journal, vol. 18, No. 11, 1999, pp. 3090-3100.

Kornberg et al., *Chromatin-modifying and -remodeling complexes*, Current Opinion in Genetics & Development, vol. 9, 1999, pp. 148-151.

Koshy et al., *Increased Expression of CD40 Ligand on Systemic Lupus Erythematosus Lymphocytes*. J. Clin. Invest, vol. 98, No. 3, Aug. 1996, pp. 826-837.

Kouzarides, *Histone acetylases and deacetylases in cell proliferation*, Current Opinion in Genetics & Development, vol. 9, 1999, pp. 40-48.

Kwon et al., *Depudecin induces morphological reversion of transformed fibroblasts via the inhibition of histone deacetylase*, Proc. Natl. Acad. Sci. USA, vol. 95, Mar. 1998, pp. 3356-3361.

Lea et al., *Discordant effects of butyrate analogues on erythroleukemia cell proliferation, differentiation and histone deacetylase*, Anticancer Res, vol. 15, No. 3, May-Jun. 1995, pp. 879-883.

Lea et al., *PubMed Abstract, Induction of histone acetylation and growth regulation in erythroleukemia cells by 4-phenylbutyrate and structural analogs*, Anticancer Res, vol. 19, No. 3A, May-Jun. 1999, pp. 1971-1976.

McBain et al., *Apoptotic Death in Adenocarcinoma Cell Lines Induced by Butyrate and Other Histone Deacetylase Inhibitors*, Biochemical Pharmacology, vol. 53, 1997, pp. 1357-1368.

Nakajima et al., *FR901228, a Potent Antitumor Antibiotic, is a Novel Histone Deacetylase Inhibitor*, Experimental Cell Research, vol. 241, 1998, pp. 126-133.

Ohno et al., *Macrophage Inflammatory Protein-2: Chromosomal Regulation in Rate Small Intestinal Epithelial Cells*, Proc. Natl. Acad. Sci. USA, vol. 94, Sep. 1997, pp. 10279-10284.

Qiu et al., *Histone Deacetylase Inhibitors Trigger a G2 Checkpoint in Normal Cells That is Defective in Tumor Cells*, Molecular Biology of the Cell, vol. 11, Jun. 2000, pp. 2069-2083.

Richon et al., *A class of hybrid polar inducers of transformed cell differentiation inhibits histone deacetylases*, Proc. Natl. Acad. Sci. USA, vol. 95, Mar. 1998, pp. 3003-3007.

Saito et al., *A synthetic Inhibitor of histone deacetylase, MS-27-275, with marked in vivo antitumor activity against human tumors*, Proc. Natl. Acad. Sci. USA, vol. 96, apr. 1999, pp. 4592-4597.

Su et al., *Abstract, A Novel Histone Deacetylase Inhibitor Identified by High-Throughput Transcriptional Screening of a Compound Library*, Cancer Research, vol. 60, Jun. 15, 2000, pp. 3137-3142.

Sun et al., *A General Requirement for the Sin3-Rpd3 Histone Deacetylase Complex in Regulating Silencing in Saccaromyces cerevisiae*, Genetics, vol. 152, Jul. 1999, pp. 921-932.

Taunton et al., *A mammalian histone deacetylase related to the yeast transcriptional regulator Rpd3p*, Science, Washington, Apr. 19, 1996.

Taunton et al., *Synthesis of Natural and Modified Trapoxins, Useful Reagents for Exploring Histone Deacetylase Function,*, J. Am. Chem. Soc., vol. 118, 1996, pp. 10412-10422.

Wang et al., *PubMed Abstract, Inhibitors of histone deacetylase relieve ETO-mediated repression and induce differentiation of AML1-ETO leukemia cells*, Cancer Res, vol. 59, No. 12, Jun. 15, 1999, pp. 2766-2769.

Yang et al., *Efficacy of a pure compound H1-A extracted from Cordyceps sinensis on autoimmune disease of MRL lpr/lpr mice*, J. Lab. Clin. Med., vol. 134, No. 5, 1999, pp. 492-500.

Yoshida et al., *Potent and Specific Inhibition of Mammalian Histone Deacetylase Both in Vivo and in Vitro by Trichostatin A*, The Journal of Biological Chemistry, vol. 265, No. 28, Oct. 5, 1990, pp. 17174-17179.

Yoshida et al., *PubMed Abstract, Trichostatin and leptomycin, Inhibition of histone deacetylation and signal-dependent nuclear export*, Ann N Y Acad Sci, vol. 886, 1999, pp. 23-36.

Yoshida et al., *Trichostatin A and trapoxin: novel chemical probes for the role of histone acetylation in chromatin structure and function*, BioEssays, vol. 17, No. 5, 1995, pp. 423-430.

International Search Report, PCT/US01/43871, Sep. 18, 2002.

Andoh et al. *Sodium butyrate enhances complement-mediated cell injury via down-regulation of decay-accelerating factor expression in colonic cancer cells*, Cancer immunology immunotherapy, vol. 50, 2002, pp. 663-672.

Nancey et al. *Butyrate strongly inhibits in vitro stimulated release of cytokines in blood*, Digestive Diseases and Sciences, vol. 47, No. 4, 2002, pp. 921-928.

Saemann et al. *Anti-inflammatory effects of sodium butyrate on human monocytes: potent inhibition of IL-12 and up-regulation of IL-10 production*, The FASEB Journal, vol. 14, 2000, pp. 2380-2382.

Sugimoto et al. *Effects of a new anti-rheumatic drug KE-298 and its active metabolite: KE-758 on secretion of thioredoxin and on the level of intracellular glutathione in human monocytes and T cells*, Molecular Immunology, vol. 38, 2001, pp. 793-799.

Dangond et al., "Differential expression of human histone deaceytlase mRNAs in response to immune cell apoptosis induction by Trichostatin A and Butyrate" *Biochem. Biophys. Res. Comm.* 247: 833-837 (1998).

Application from related application (filing receipt attached). Kammer et al., *Method of Treating Autoimmune Diseases*, U.S. Appl. No. 11/403,608, filed Apr. 13, 2006.

Application from related application (filing receipt attached). Kammer et al., *Method of Treating Autoimmune Disease*, U.S. Appl. No. 09/718,195, filed Nov. 20, 2000.

* cited by examiner

METHOD OF TREATING AUTOIMMUNE DISEASES

CROSS REFERENCE TO RELATED APPLICATION

The present application is a continuation-in-part of U.S. application Ser. No. 09/718,195, filed Nov. 20, 2000, now abandoned, is a continuation of which and claims priority from PCT Application No. PCT/US01/43871, filed Nov. 19, 2001, the disclosures of both of which are incorporated herein by reference in their entirety.

STATEMENT OF FEDERAL SUPPORT

This invention was made possible with government support under grant numbers R01 AR39501 from the National Institute of Health. The United States government may have certain rights to this invention.

FIELD OF THE INVENTION

The present invention relates to methods for the treatment of autoimmune diseases such as systemic lupus erythematosus or rheumatoid arthritis.

BACKGROUND OF THE INVENTION

The hallmark of the aberrant cellular immune response in systemic lupus erythematosus (SLE) is T cell dysfunction (A. K. Dayal and G. M. Kammer, *Arthritis Rheum.* 39, 23 (1996); D. A. Horwitz, et al., in *Dubois'Lupus Erythematosus*., D. J. Wallace and B. H. Hahn, Eds. (Williams & Wilkins, Baltimore, 1997), chap. 10). An imbalance exists between exaggerated helper function and deficient cytotoxic/suppressor activity that promotes inappropriate B cell overproduction of immunoglobulins (Ig). The resulting polyclonal hypergammaglobulinemia is comprised of natural antibodies and pathogenic autoantibodies, including anti-native DNA. Formation of complement-fixing immune complexes in situ or their deposition on vascular endothelium, such as the renal glomerulus, initiates a chronic inflammatory response that leads to irreparable parenchymal damage, ultimately resulting in end-organ failure (R. P. Kimberly, in *Arthritis and Allied Conditions: A Textbook of Rheumatology*, W. J. Koopman, Ed. (Williams & Wilkins, Baltimore, 1997) chap. 27). Moreover, T cell dysfunctions predispose to recurrent, often life-threatening infections. See, A. G. Iliopoulos and G. C. Tsokos, *Sem. Arthritis Rheum.* 25, 318 (1996); C. A. Hunter and S. L. Reiner, *Curr. Opin. Immunol.* 12, 413 (2000).

Two principal defects of T cell function in SLE are augmented expression of cell surface receptors and altered production of cytokines. CD40 ligand (CD154) expression is significantly increased and prolonged on both $CD4^+$ helper (Th) and $CD8^+$ cytotoxic/suppressor (Tc) subpopulations (M. Koshy, et al., *J. Clin. Invest.* 98, 826 (1996); A. Desai-Mehta, et al, *J. Clin. Invest.* 97, 2063 (1996)). This prolonged over-expression may be pathophysiologically significant, for binding of CD154 on Th cells to CD40 on B cells promotes B cell activation and may drive the polyclonal hypergammaglobulinemia. Moreover, Th2 cells over-produce IL-10 whereas Th1 cells under-produce IFN-γ. Heightened levels of IL-10 may profoundly modify the cellular immune response by (a) downregulating both IFN-γ and IL-2 production by Th1 cells; (b) inhibiting IL-12 generation and down-regulating expression of IL-12 receptors on Th1 cells; (c) up-regulating bcl-2 expression and preventing apoptosis of activated T cells; and, (d) promoting B cell growth, differentiation and autoantibody production. By contrast, deficient IFN-γ may significantly hinder cellular immunity in SLE by both impairing Tc-dependent cytotoxicity and altering antigen-presentation (B. S. Handwerger, et al., in *Lupus: Molecular and Cellular Pathogenesis*, G. M. Kammer and G. C. Tsokos, Eds. (Humana Press, Totowa, N.J., 1999), chap. 21).

Histone deacetylases (HDACs) are enzymes that deacetylate specific lysine residues of histone amino-terminal tail domains and certain non-histone substrates. Current evidence implicates the deacetylases in transcriptional repression (T. Kouzarides, *Curr. Opin. Genet. Dev.* 9, 40 (1999); W. D. Cress and E. Seto, *J. Cell. Physiol.* 184, 1 (2000)). Complexed with Sin3 and Mi2 transcriptional co-repressor proteins, HDAC/Sin3 and HDAC/Mi2 associate with other DNA-binding proteins, such as Ikaros (W. D. Cress and E. Seto, *J. Cell. Physiol.* 184, 1 (2000); J. Kim et al., *Immunity* 10, 345 (1999)). These deacetylase complexes appear to limit the accessibility of transcription factors to the promoter by closely juxtaposing the nucleosome to DNA. Of the eight human HDACs discovered (W. D. Cress and E. Seto, *J. Cell. Physiol.* 184, 1 (2000)), to date only HDACs1-3 have been identified in T cells (F. Dangond et al., *Biochem. Biophys. Res. Comm.* 242, 648 (1998)). During T cell activation, HDAC/Mi2 complexes are recruited to regions of the heterochromatin by Ikaros and modulate gene expression (J. Kim et al., *Immunity* 10, 345 (1999); Koipally, J., et al. *EMBO J* 18, 3090 (1999)). Trichostatin A, an HDAC inhibitor (M. Yoshida, et al., *J. Biol. Chem.* 265, 17174 (1990); S. Finnin et al., *Nature* 401, 188 (1999)), blocks deacetylase activity and shifts the equilibrium toward histone acetylation. By acetylating histones, chromatin is remodeled, promoting access of DNA-binding transcription factors and the transcriptional machinery to promoter/enhancer regions (W. D. Cress and E. Seto, *J. Cell. Physiol.* 184, 1 (2000); R. D. Komberg and Y. Lorch, *Curr. Opin. Gen. Dev.* 9, 148 (1999)). Acetylation may mediate positive or negative regulatory events that depend upon the particular gene (Z. W. Sun and M. Hampsey, *Genetics* 152, 921 (1999)). Thus, promoter regions that are ordinarily silenced can then be derepressed whereas those that are expressed can be repressed. However, the use of histone deacetylase inhibitors or other histone hyperacetylating agents in the treatment of autoimmune diseases such as SLE has not heretofore been suggested or disclosed.

While several treatments for autoimmune diseases such as SLE and rheumatoid arthritis have been developed, none are entirely satisfactory. Hence, there remains a need for new ways to treat autoimmune diseases.

SUMMARY OF THE INVENTION

A first aspect of the present invention is a method of treating an autoimmune disease in a subject in need thereof, comprising administering to the subject a therapeutically effective amount of a histone hyperacetylating agent, or a pharmaceutically acceptable salt thereof.

A second aspect of the present invention is a method of treating Systemic Lupus Erythematosus in a subject in need thereof, comprising administering to that subject a therapeutically effective amount of a histone hyperacetylating agent, or a pharmaceutically acceptable salt thereof.

A still further aspect of the present invention is the use of an active agent as described above for the preparation of a medicament for the treatment of a disorder as described above.

Still further aspects of the present invention are methods of treating an autoimmune disease in a subject in vivo.

Another aspect of the present invention includes methods a treating an autoimmune disease in a subject comprising the administration of a pharmaceutical formulation to the subject.

Yet another aspect of the present invention comprises administering a compound to treat an autoimmune disease.

The present invention is explained in greater detail in the specification set forth below.

BRIEF DESCRIPTION OF THE DRAWINGS

FIG. 6A is a schematic diagram of the promoter regions; FIG. 6B illustrates chromatin fragments from vehicle or TSA treated SLE PBMCs that were immunoprecipitated with normal IgG, anti-acetylated H3 or anti-acetylated H4 antibodies, and wherein PCR primer sets are for the regions indicated in lane A; FIGS. 6C and 6D are the quantitation of CHIP from SLE (C) or normal controls (D); FIG. 6E demonstrates that TSA does not change acetylated state of G6PD gene in SLE PBMCs; and FIG. 6F is the quantitation of FIG. 6E.

FIG. 8A shows that TSA decreases the levels of IFN-γ mRNA relative to GAPDH mRNA in MRL/lpr splenocytes; FIG. 8B shows that TSA and SAHA prevent induction of IFN-γ mRNA by Con A; FIG. 8C indicates a fold change of IFN-γ mRNA shown in FIG. 8B; and FIG. 8D is a graph depicting the amount of IFN-γ protein secretion, wherein the bar represents the mean±SEM of three independent experiments.

FIG. 9E depicts the amount of IL-12 p40 protein secretion.

FIG. 13A illustrates the semiquantitative RT-PCR of iNOS in MRL/lpr splenocytes, and FIG. 13B illustrates the production of nitric oxide from MRL/lpr mesangial cells, respectively.

DETAILED DESCRIPTION OF PREFERRED EMBODIMENTS

Figure 1A:
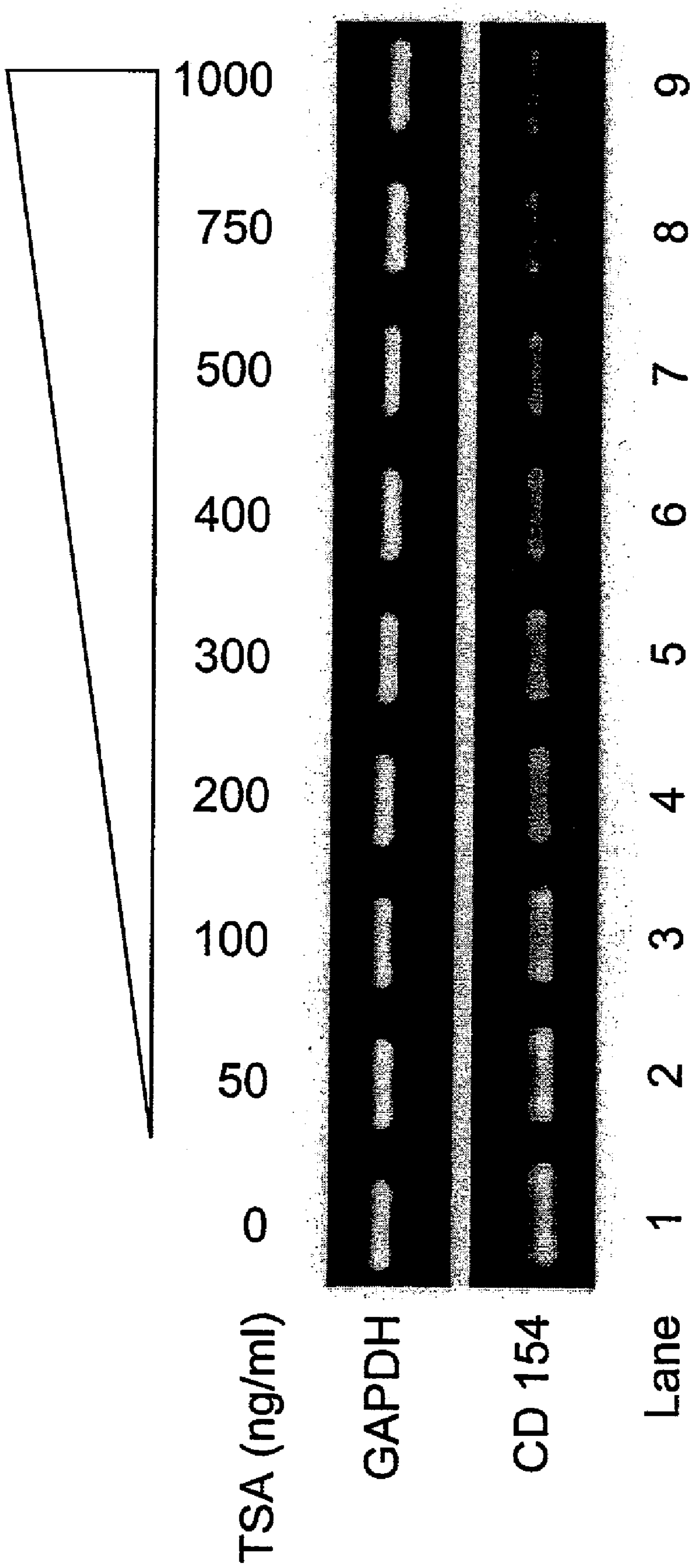
FIG. 1A illustrates the down-regulation of CD154 transcript levels by trichostatin A (TSA). Increasing concentrations of TSA (0–1000 ng/ml) progressively inhibit expression of CD154 mRNA relative to expression of GAPDH mRNA.

The term "treat" as used herein refers to any type of treatment that imparts a benefit to a patient afflicted with a disease, including improvement in the condition of the patient (e.g., in one or more symptoms), delay in the progression of the disease, etc.

The phrase "pharmaceutically acceptable" as used herein means that the compound or composition is suitable for administration to a subject to achieve the treatments described herein, without unduly deleterious side effects in light of the severity of the disease and necessity of the treatment.

A "therapeutically effective" amount as used herein is an amount of a histone hyperacetylating agent that is sufficient to treat autoimmune diseases in a subject. The therapeutically effective amount will vary with the age and physical condition of the patient, the severity of the treatment, the duration of the treatment, the nature of any concurrent treatment, the pharmaceutically acceptable carrier used and like factors within the knowledge and expertise of those skilled in the art.

Active compounds of the present invention may optionally be administered in conjunction with other compounds useful in the treatment of the autoimmune disease such as SLE. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "concurrently" or "in combination" means that the two compounds are administered closely enough in time that the presence of one alters the biological effects of the other. The two compounds may be administered simultaneously or sequentially. Simultaneous administration may be carried out by mixing the compounds prior to administration, or by administering the compounds at the same point in time but at different anatomic sites or using different routes of administration.

Autoimmune diseases with which the present invention is concerned include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, Behcet's Disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, CREST syndrome, cold agglutinin disease, Crohn's disease, discoid lupus, essential mixed cryoblobulinemia, fibromyalgia, fibromyositis, Goodpasture syndrome, graft versus host disease, Grave's disease, Guillain-Barre syndrome, Hashimoto's thyroiditis, idiopathic pulmonary fibrosis, idiopathic thrombocytopenia purpura, IgA nephropathy, insulin dependent diabetes, juvenile arthritis, lichen planus, lupus, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis, dermatomyositis, primary agammaglobulinemia, primary biliary cirrhosis, psoriasis, Raynaud's Phenomenon, Reiter's syndrome, rheumatic fever, sarcoidosis, scleroderma, Sjogren's syndrome, Stiff-Man syndrome, Takayasu Arteritis, temporal arteritis, giant cell arteritis, ulcerative colitis, uveitis, vasculitis, vitiligo and Wegener's granulomatosis. A particularly preferred application of the present invention is in the treatment of systemic lupus erythematosus (SLE).

The present invention is primarily concerned with the treatment of human subjects, but the invention may also be carried out on animal subjects, particularly mammalian subjects such as mice, rats, dogs, cats, livestock and horses for veterinary purposes, and in vitro for drug screening and drug development purposes. In addition, the present invention may be used to treat animal subjects that are models of an autoimmune disease for drug screening and development purposes. A particular example of such a model is the mouse NZB/NZW F1 model of SLE.

Active Compounds

Active compounds used to carry out the present invention are, in general, histone hyperacetylating agents, such as histone deacetylase inhibitors. Numerous such compounds are known. See, e.g., P. Dulski, Histone Deacetylase as Target for Antiprotozoal Agents, PCT Application WO 97/11366 (27, Mar. 1997). Examples of such compounds include, but are not limited to:

Trichostatin and its analogues, such as: Trichostatin A (TSA); and Trichostatin C (Koghe et al. 1998. *Biochem. Pharmacol.* 56:1359–1364).

Peptides, such as: Oxamflati [(2E)-5-[3-[(phenylsufonyl) amino phenyl1]-pent -2-en-4-ynohydroxamic acid (Kim et al., *Oncogene,* 18:2461–2470 (1999)); Trapoxin A (TPX)-Cyclic Tetrapeptide (cyclo-(L-phenylalanyl-L-phenylalanyl-D-pipecolinyl-L-2-amino -8-oxo-9,10-epoxy-decanoyl)) (Kijima et al., *J. Biol. Chem.* 268, 22429–22435 (1993)); FR901228, Depsipeptide (Nakajima et al., *Ex. Cell Res.* 241, 126–133 (1998)); FR225497, Cyclic Tetrapeptide (H. Mori et al., PCT Application WO 00/08048 (17, Feb. 2000)); Apicidin, Cyclic Tetrapeptide [cyclo(N-O-methyl-L-tryptophanyl-L-isoleucinyl -D-pipecolinyl-L-2-amino-8-oxodecanoyl)] (Darkin-Rattray et al., *Proc. Natl. Acad. Sci. USA* 93, 13143–13147 (1996)); Apicidin 1a, Apicidin Ib, Apicidin Ic, Apicidin IIa, and Apicidin IIb (P. Dulski et al., PCT Application WO 97/11366); HC-Toxin, Cyclic Tetrapeptide (Bosch et al., *Plant Cell* 7, 1941–1950 (1995)); WF27082, Cyclic Tetrapeptide (PCT Application WO 98/48825); and chlamydocin (Bosch et al., supra).

Hydroxamic Acid-Based Hybrid Polar Compounds (HPCs), such as: Salicylihydroxamic Acid (SBHA) (Andrews et al., *International J. Parasitology* 30, 761–768 (2000)); Suberoylanilide Hydroxamic Acid (SAHA) (Richon et al., *Proc. Natl. Acad. Sci. USA* 95, 3003–3007 (1998)); Azelaic Bishydroxamic Acid (ABHA) (Andrews et al., supra); Azelaic-1-Hydroxamate-9-Anilide (AAHA) (Qiu et al., *Mol. Biol. Cell* 11, 2069–2083 (2000)); M-Carboxycinnamic Acid Bishydroxamide (CBHA) (Ricon et al., supra); 6-(3-Chlorophenylureido)carpoic Hydroxamic Acid (3-Cl-UCHA) (Richon et al., supra); MW2796 (Andrews et al., supra); and MW2996 (Andrews et al., supra). Note that analogs not effective as HDAC Inhibitors are: Hexamethylene bisacetamide (HBMA) (Richon et al. 1998, PNAS, 95:3003–3007); and Diethyl bix(pentamethylene-N,N-dimethylcarboxamide) malonate (EMBA) (Richon et al. 1998, PNAS, 95:3003–3007).

Short Chain Fatty Acid (SCFA) Compounds, such as: Sodium Butyrate (Cousens et al., *J. Biol. Chem.* 254, 1716–1723 (1979)); Isovalerate (McBain et al., *Biochem. Pharm.* 53:1357–1368 (1997)); Valerate (McBain et al., supra); 4-Phenylbutyrate (4-PBA) (Lea and Tulsyan, *Anticancer Research,* 15, 879–873 (1995)); Phenylbutyrate (PB) (Wang et al., *Cancer Research,* 59, 2766–2799 (1999)); Propionate (McBain et al., supra); Butrymide (Lea and Tulsyan, supra); Isobutyramide (Lea and Tulsyan, supra); Phenylacetate (Lea and Tulsyan, supra); 3-Bromopropionate (Lea and Tulsyan, supra); and Tributyrin (Guan et al., *Cancer Research,* 60, 749–755 (2000)).

Benzamide derivatives, such as: MS-27-275 [N-(2-aminophenyl)-4-[N-(pyridin-3-yl-methoxycarbonyl) aminomethyl]benzamide] (Saito et al., *Proc. Natl. Acad. Sci. USA* 96, 4592–4597 (1999)); and 3'-amino derivative of MS-27-275 (Saito et al., supra).

Other inhibitors, such as: Depudecin [its analogues (mono-MTM-depudecin and depudecin-bisether) do not inhibit HDAC) (Kwon et al. 1998. PNAS 95:3356–3361); and Scriptaid (Su et al. 2000 Cancer Research, 60:3137–3142). Additionally, other inhibitors, such as: isoquinolins which would include scriptaid and nullscipt.

The compounds may include the general formula:

Formula (I)

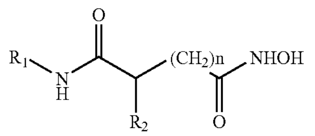

wherein each of $R_1$ and $R_2$ is, substituted or unsubstituted, hydrogen, aryl, cycloalkyl, cycloalkylamino, naphtha, pyridineamino, piperidino, t-butyl, aryloxy, arylalkoyloxy, phenyl or pyridine group; and wherein $R_2$ may be attached by a linker such as an amido moiety, —O—, —S—, —NH— or —$CH_2$—; and wherein n is an integer from 3 to 8.

The active compounds disclosed can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Compounds for Concurrent Administration

The active compound histone hyperacetylating agents described herein may be administered concurrently with other active compounds known for the treatment of autoimmune diseases (such as systemic lupus erythematosus). Examples of such other active compounds include, but are not limited to: (i) corticosteroids such as prednisolone sodium phosphate, such as Pediapred®; methylprednisolone, such as Medrole®; prednisone, such as Deltasone® or Orasone®; and dexamethasone, such as Decadron® Tablets; (ii) steroids such as lynestrenol—a progestagen; desogestrel—a progestagen; ethylestrenol—an anabolic steroid; and tibolone—a weak progestational, anabolic, androgenic steroid (H. A. Verheul et al. *Clin. Immunol. Immunopathol.* 38:198–208 (1986)); and exogenous DHEA—dehydroepiandrosterone—(T. Suzuki et al. *Clin. Exp. Immunol.* 99:251–255 (1995)); and (iii) other compounds such as hydroxchloroquine sulfate, such as Plaquenil®; H1-A (isolated from Cordyceps sinensis) (L. Y. Yang, et al. *J. Lab Clin. Med.* 134:492–500 (1999)); sulfasalazine (a.k.a. Salazosulfapyridine) (E. Delaporte et al. *Ann. Dermatol. Venereol.* 124:151–156 (1997)); anti-ICAM-1—murine antiintercellular adhesion molecule-1 (R. L. Brey et al. *Lupus* 6:645–651 (1997)); MX-68—upolyglutamable antifolate (M. Mihara et al. *Int. Arch. Allergy Immunol.* 13:454–459 (1997)); FK506—(K. Yamamoto et al. *Immunology* 69:222–227 (1990)); AS101—organotellurium compound—(J. Alcocer-Varela et al. *Clin. Exp. Immunol.* 77:319–323 (1989)); HWA-131—(3-(3,5-ditert.butyl-4-hydroxyphenyl)-7H-thiazolo(3,2-b) (1,2,4)triaz in-7-one) (R. R. Bartlett et al. *Drugs Exp. Clin. Res.* 15:521–526 (1989)); and Auranofin—Oral gold compound—(K. Dalziel et al. *Br. J. Dermatol.* 115:211–216 (1986)).

The foregoing may be administered in the same formulation and/or by the same route of administration, or by a different formulation and/or different route of administration, as the active agent histone hyperacetylating agents described herein, in their conventional dosages or dosages which can be determined from the conventional dosages.

Pharmaceutical Formulations

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, intraperitoneal, intravenous, etc.), topical (e.g., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound as described above, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary from compound to compound and patient to patient, and will depend upon factors such as the age, weight, gender and condition of the patient and the route of delivery. As a general proposition, a dosage from about 0.01 or 0.1 to about 50, 100 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 0.01 mg/kg to 50 mg/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the disorder, or the severity of symptoms. For example, the trichostatin analog SAHA is being given in phase I clinical trials for cancer by an intravenous route Screening Assays The present invention also provides screening assays for identifying compounds useful, or potentially useful, in the treatment of autoimmune diseases such as SLE. Such assays may be carried out in accordance with known techniques, such as the formats described in P. Dulski, PCT Application WO97/11366 (27, Mar. 1997).

One method of screening compounds for activity in treating an autoimmune disease, comprises: contacting a histone deacetylase, or an extract containing histone deacetylase with (i) a known amount of a labeled compound that interacts with a histone deacetylase; and (ii) a known dilution of a test compound or natural product extract; and then determining the inhibition of interaction of said labeled compound with said histone deacetylase induced by said test compound, where the inhibition of interaction of said labeled compound with said histone deacetylase indicates said compound or extract is a candidate for the treatment of an autoimmune disease.

The histone deacetylase is preferably a mammalian (e.g., mouse, rat, rabbit) histone deacetylase, and is most preferably a human histone deacetylase. The labeled compound may be any of the active agents described above, labeled with a suitable detectable group such as tritium. In general, the labeled compound will be one which binds to histone deacetylase or is a substrate of histone deacetylase. The test compound may be of any source, such as an oligomer or a non-oligomer from a combinatorial library, or a rationally synthesized candidate compound. Extracts may be obtained from any suitable source, such as plant extracts obtained through techniques known in traditional, folk or herbal medicine. The determining step may be carried out qualitatively or quantitatively by any suitable means, such as by Scatchard analysis with a series of serial dilutions of the test compound or extract.

In another embodiment, a method of screening compounds for activity in treating an autoimmune disease such as SLE comprises: contacting an intact host cell in vivo or in vitro with a test compound or a natural product extract; and then determining the level of histone acetylation in said cell, wherein elevated levels of histone acetylation indicates said compound or extract is a candidate for the treatment of an autoimmune disease.

Where the contacting step is carried out in vivo (e.g., as in the course of a clinical trial) the compound is administered to a suitable subject carrying the cell by any of the same techniques described above for administering active agents, and the cell (or collection of cells) subsequently collected from the subject for use in the determining step. The cell (or subject) is preferably mammalian (e.g., a mouse, rat or rabbit cell) and in one particularly preferred embodiment is human. Lymphocytes are particularly preferred cells. The subject may be one afflicted with an autoimmune disease such as SLE (including models of such a disease), or may be a normal (or unafflicted) subject. Elevated levels may be determined by comparison to an untreated, control subject or cell, by comparison to levels found in the same subject or cell or cell population prior to treatment, etc. Assays for histone levels may be carried out by any suitable technique, with histone level assays being known to those skilled in the art.

The examples, which follow, are set forth to illustrate the present invention, and are not to be construed as limiting thereof. In the following examples, hr means hour; min means minute; TSA means Trichostatin A; SLE means systemic lupus erythematosus; RT-PCR means reverse transcriptase polymerase chain reaction; IO means ionomycin, PMA means phorbol myristate acetate, ml means milliliter; ng means nanogram; and all temperatures, unless otherwise indicated, are in degrees Celsius.

EXAMPLE 1

Down-Regulation of CD154 Transcript and Protein Levels by TSA

Because SLE T cells are often activated (D. T. Y. Yu et al., *J. Exp. Med.* 151, 91 (1980).), the up-regulation of CD154 and IL-10 and down-regulation of IFN-γ may reflect skewed gene expression due to enhanced recruitment of HDACs to the promoters of these genes. The resulting disequilibrium of acetylation might be expected to alter the chromatin structure of the promoters (R. D. Komberg and Y. Lorch, *Curr. Opin. Gen. Dev.* 9, 148 (1999)), thereby activating previously silenced genes while repressing expressed genes. To determine if TSA can down-regulate CD154 transcript expression, T cells from eight SLE subjects were treated with increasing concentrations of TSA over 18 hr.

T cells were cultured in the absence or presence of increasing concentrations of TSA for 18 hr in 5% $CO_2$ at 37° C. RNA was isolated, cDNAs were prepared, and RT-PCR was performed as previously detailed (D. Laxminarayana, et al., *J. Clin. Invest.* 92, 2207 (1993)). The primers used were:

```
CD154:
5'-GAATCCTCAAATTGCGGCAC-3'and          (SEQ ID NO:1)
5'-CAGAAGGTGACTTGGCATAG-3';            (SEQ ID NO:2)

GAPDH:
5'-GGTGAAGGTCGGAGTCAACG-3'and          (SEQ ID NO:3)
5'-CAAAGTTGTCATGGATGACC-3';            (SEQ ID NO:4)

IL-10:
5'-TTGCCTGGTCCTCCTGACTG-3'and          (SEQ ID NO:5)
5'-GATGTCTGGGTCTTGGTTCT-3';            (SEQ ID NO:6)
```

-continued

```
IFN-γ:
5'-ATGAAATATACAAGTTATATCTTGGCTTT-3'and (SEQ ID NO:7)
5'-GATGCTCTTCGACCTCGAAACAGCAT-3'.      (SEQ ID NO:8)
```

The reaction mixtures were subjected to 30 cycles of denaturation (94° C., 1 min) and annealing for 1 min at 53° C. (CD154), 40° C. (GAPDH) and 55° C. (IL-10 and IFN-γ). Extension was for 2 min at 72° C. with a final extension of 7 min at 72° C. using a DNA thermal cycler (Perkin-Elmer).

Figure 1B:
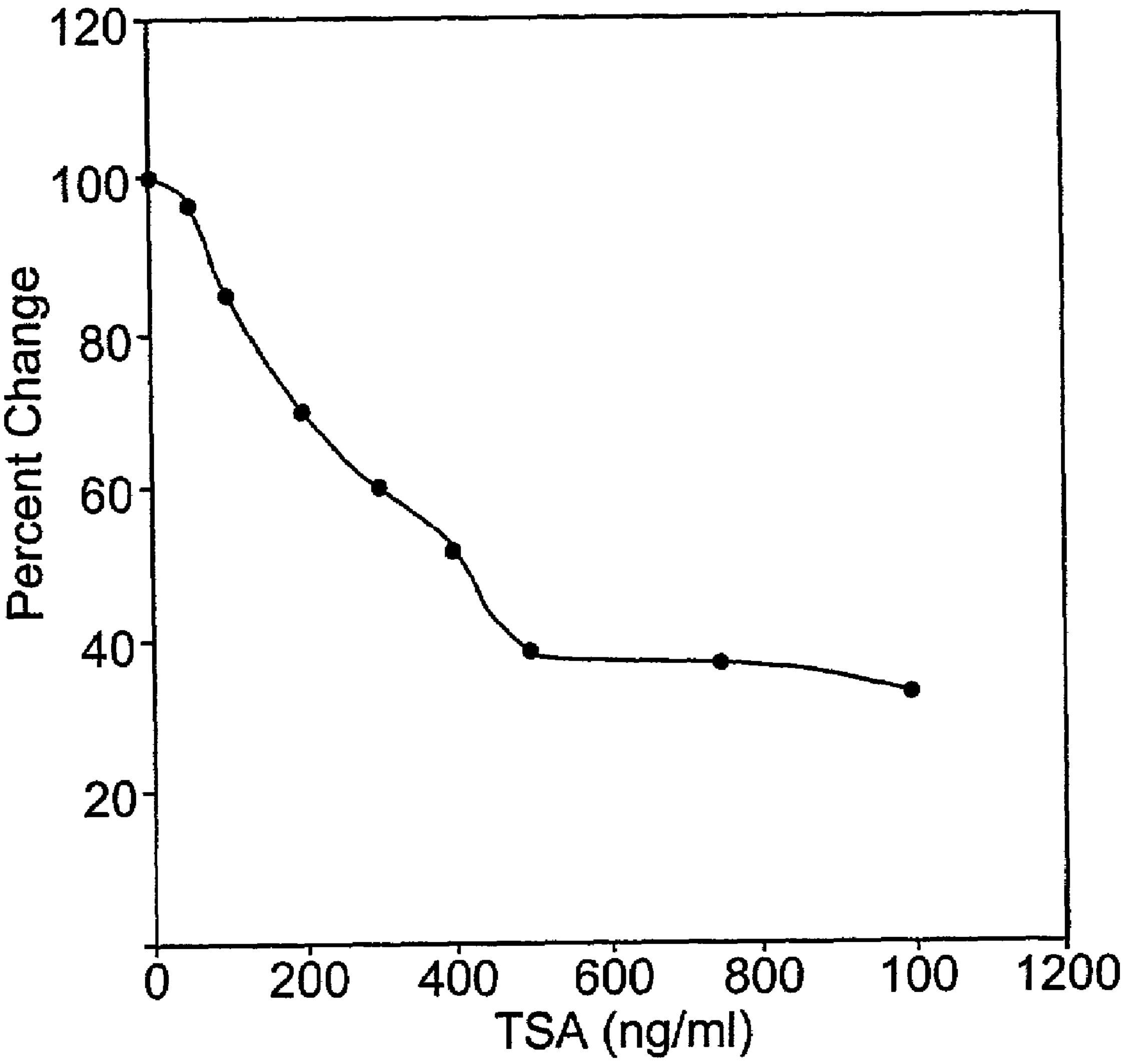
FIG. 1B shows a graphic depiction of a densitometric scan of the gel in FIG. 1A. This graph depicts the percent change of CD154 mRNA expression with increasing concentrations of TSA over 24 hr. GAPDH mRNA expression is stable and unchanged in the presence of TSA.
Figure 1C:
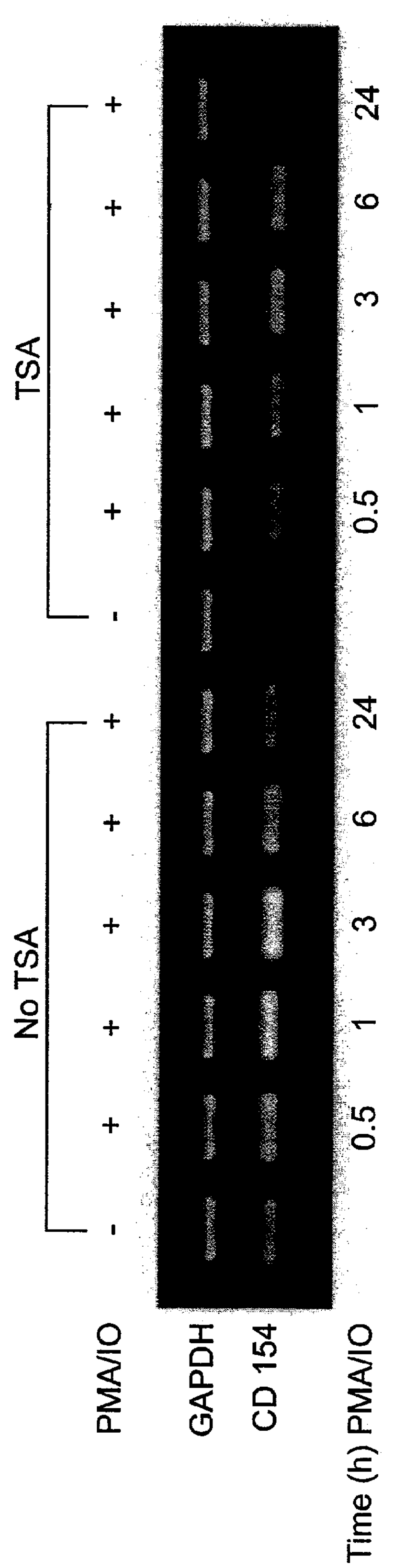
FIG. 1C illustrates CD154 transcript levels in T cells incubated in the absence or presence of 1000 ng/ml TSA over 18 hr. T cells were then stimulated with 20 ng/ml PMA+0.5 μM IO for intervals to 24 hr. CD154 mRNA expression relative to GAPDH mRNA expression is shown.
Figure 1D:
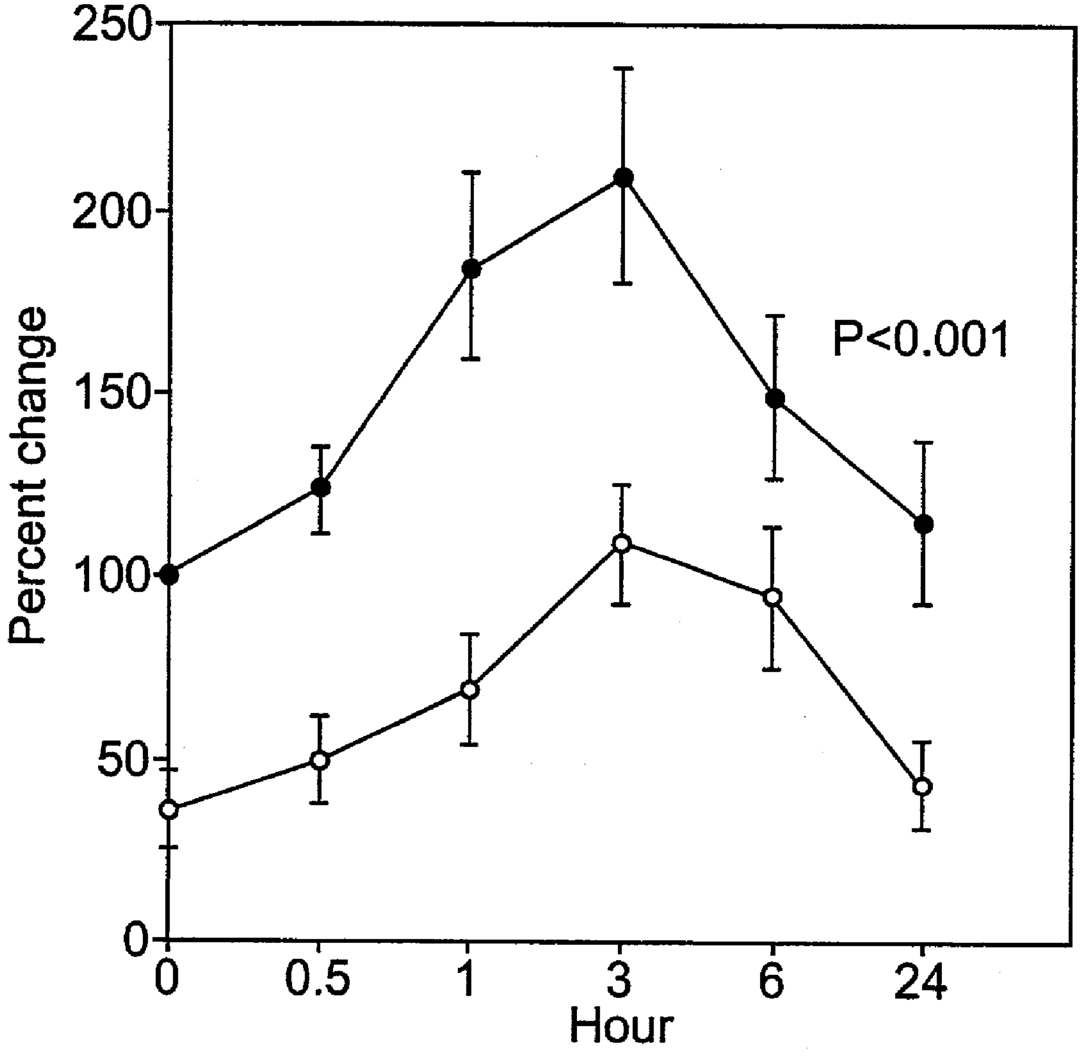
FIG. 1D shows a graphic depiction of the percent change in CD154 mRNA expression over time in the absence (filled circles) or presence (open circles) of TSA.

FIGS. 1A and 1B demonstrate that TSA maximally inhibits CD154 transcript by 60%, but does not modify GAPDH mRNA expression. When SLE T cells were activated with phorbol myristate acetate (PMA) and ionomycin (IO), CD154 mRNA content increased 100%, peaked at 3 hr, and waned thereafter (FIGS. 1C and 1D). Under these conditions, however, GAPDH mRNA remained stable, demonstrating that cellular activation also does not modify the expression of this gene. By contrast, when T cells were preincubated with TSA for 18 hr and then activated by PMA+IO over intervals to 24 hr, up-regulation of CD154 transcript was significantly reduced throughout the entire time course compared to cells not exposed to TSA (FIGS. 1C and 1D; P<0.001). Thus, in SLE T cells TSA significantly down-regulates CD154 transcript expression.

Figure 1E:
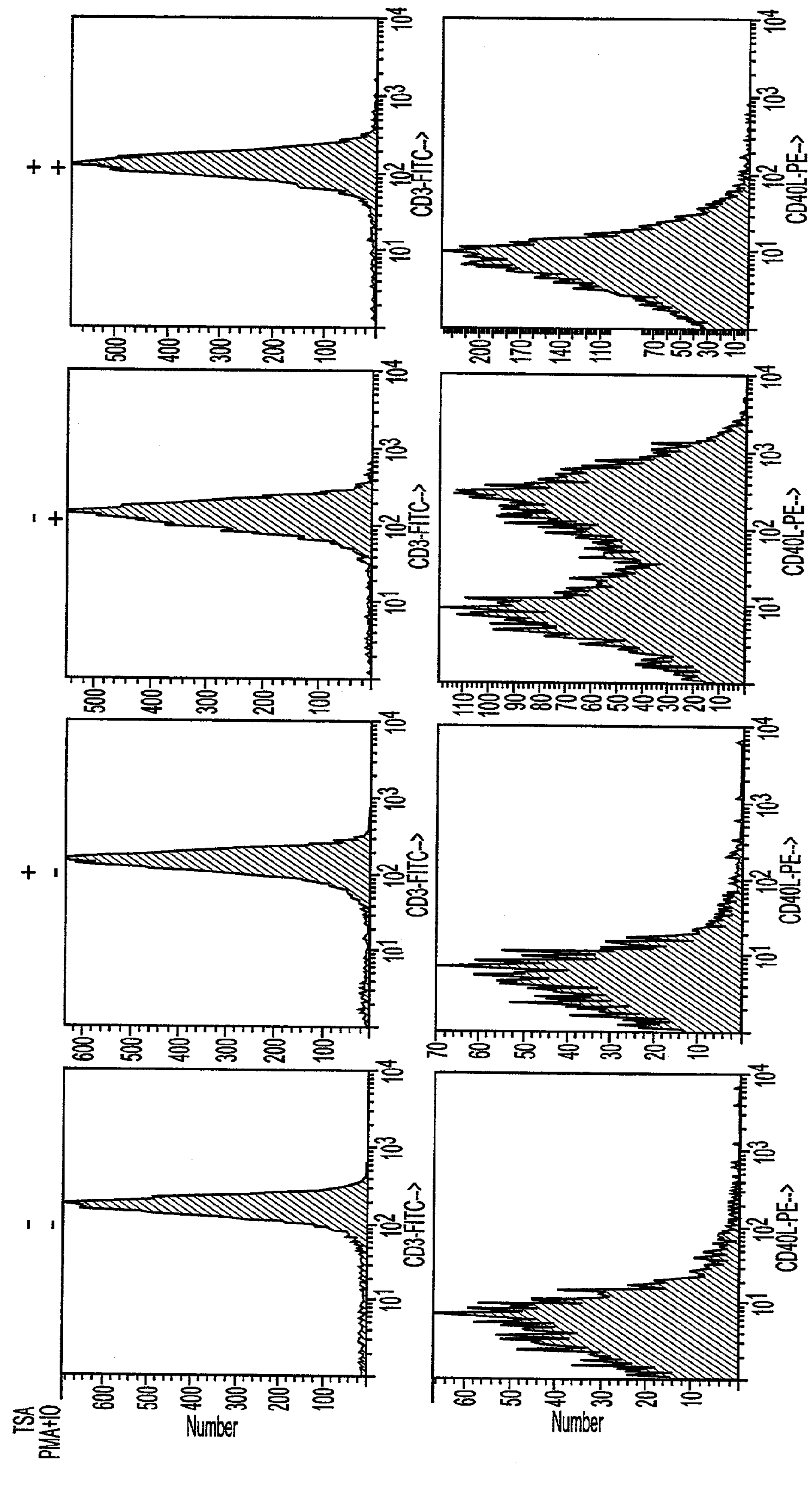
FIG. 1E demonstrates flow cytometric analysis of CD154 and CD3-ϵ expression on SLE T cells. T cells were cultured in the absence or presence of 1000 ng/ml TSA for 18 hr, and subsequently activated with 20 ng/ml PMA+0.5 μMIO for 24 hr. The abscissa denotes the number of cells and ordinate the intensity of cell fluorescence signal. Statistical analyses were performed by paired Student's t test or one-way ANOVA.

In agreement with previous work (M. Koshy, et al., *J. Clin. Invest.* 98, 826 (1996); A. Desai-Mehta, et al., *J. Clin. Invest.* 97, 2063 (1996)), we find that an increased proportion of SLE T cells express cell-surface CD154 compared to normal and disease controls. To determine if TSA-dependent down-regulation of CD154 mRNA reduces surface expression of CD154, SLE T cells were treated for 18 hr with TSA and the proportion of $CD154^+$ cells quantified by flow cytometry (E. Hagiwara, et al., *Arthritis Rheum.* 39, 379 (1996)). Compared with untreated cells, TSA did not effect any significant reduction of cell-surface $CD154^+$ cells over 24 hr (FIG. 1E). However, activation of SLE T cells with PMA+IO over 24 hr induced a new population of $CD154^+$ cells that was completely inhibited when cells were pretreated with TSA prior to activation (FIG. 1E; P=0.005). By contrast, CD3-ε expression remained stable under these varying conditions, indicating that TSA's effect on CD154 surface expression is not generalized (FIG. 1E). T cells were stained with saturating concentrations of monoclonal FITC-anti-CD3 and PE anti-CD154 antibodies (Caltag Labs, Burlingame, Calif.) for 30 min at 4° C., and the proportion of cells expressing CD3-ε and CD154 was quantified. In sum, these experiments reveal that TSA down-regulates both CD154 mRNA and protein expression, but not GAPDH mRNA or CD3-ε expression, in SLE T cells.

EXAMPLE 2

Down-Regulation of IL-10 Transcript and Protein Levels by TSA

Figure 2A:
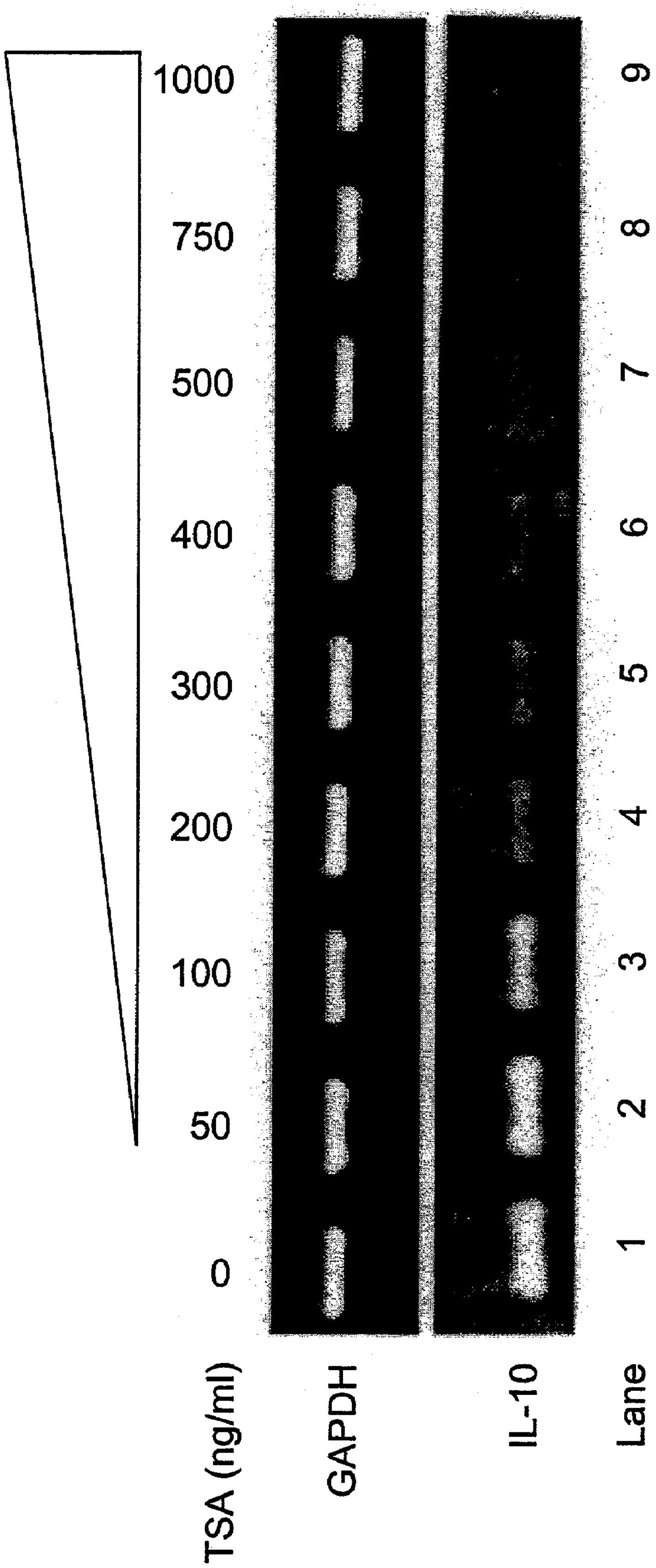
FIG. 2A depicts the down-regulation of IL-10 levels by TSA. Increasing concentrations of TSA (0–1000 ng/ml) progressively inhibit expression of IL-10 mRNA relative to expression of GAPDH mRNA.
Figure 2B:
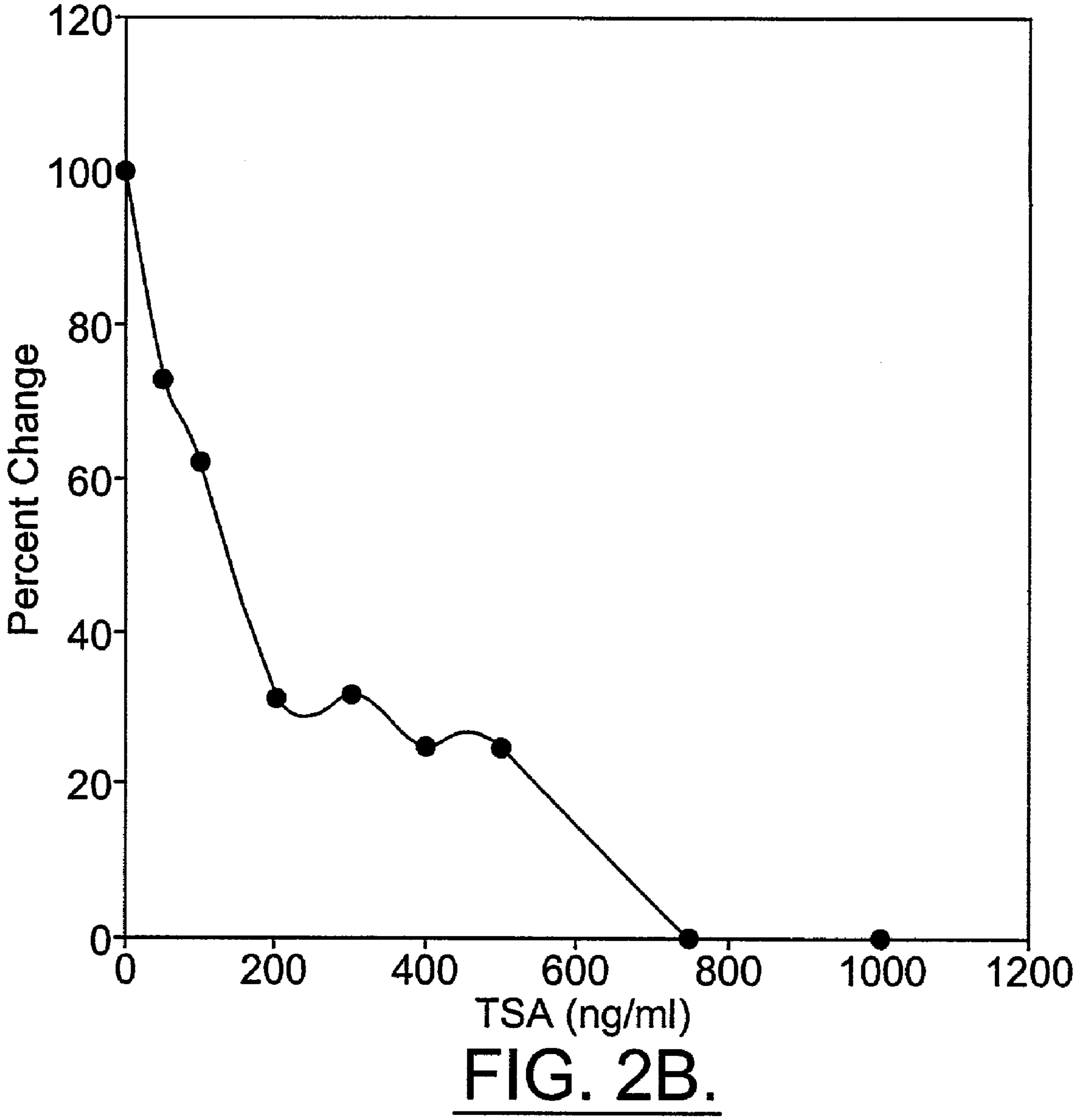
FIG. 2B shows a graphic depiction of a densitometric scan of the gel in FIG. 2A. This graph depicts the percent change of IL-10 transcript expression with increasing concentrations of TSA over 24 hr.
Figure 2C:
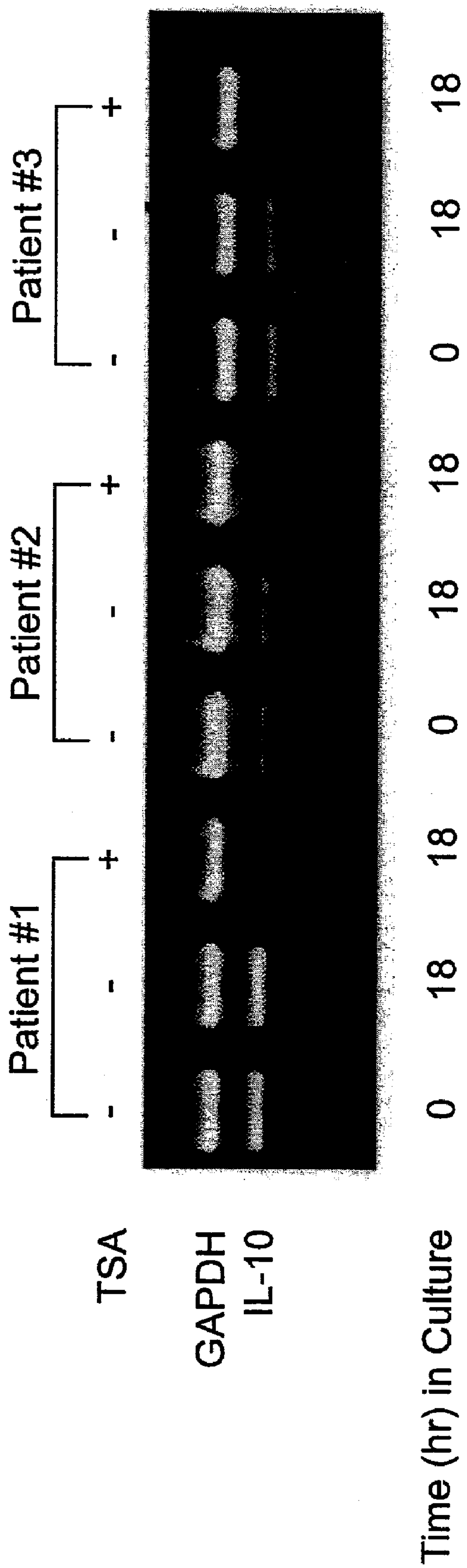
FIG. 2C shows IL-10 and GAPDH transcripts from T cells of three SLE subjects. Transcripts from freshly isolated T cells are shown in lanes 1, 4, and 7. Transcripts from T cells cultured for 18 hr in the absence or presence of 1000 ng/ml TSA are shown in lanes 2, 5, 8 and 3, 6, and 9, respectively.
Figure 2D:
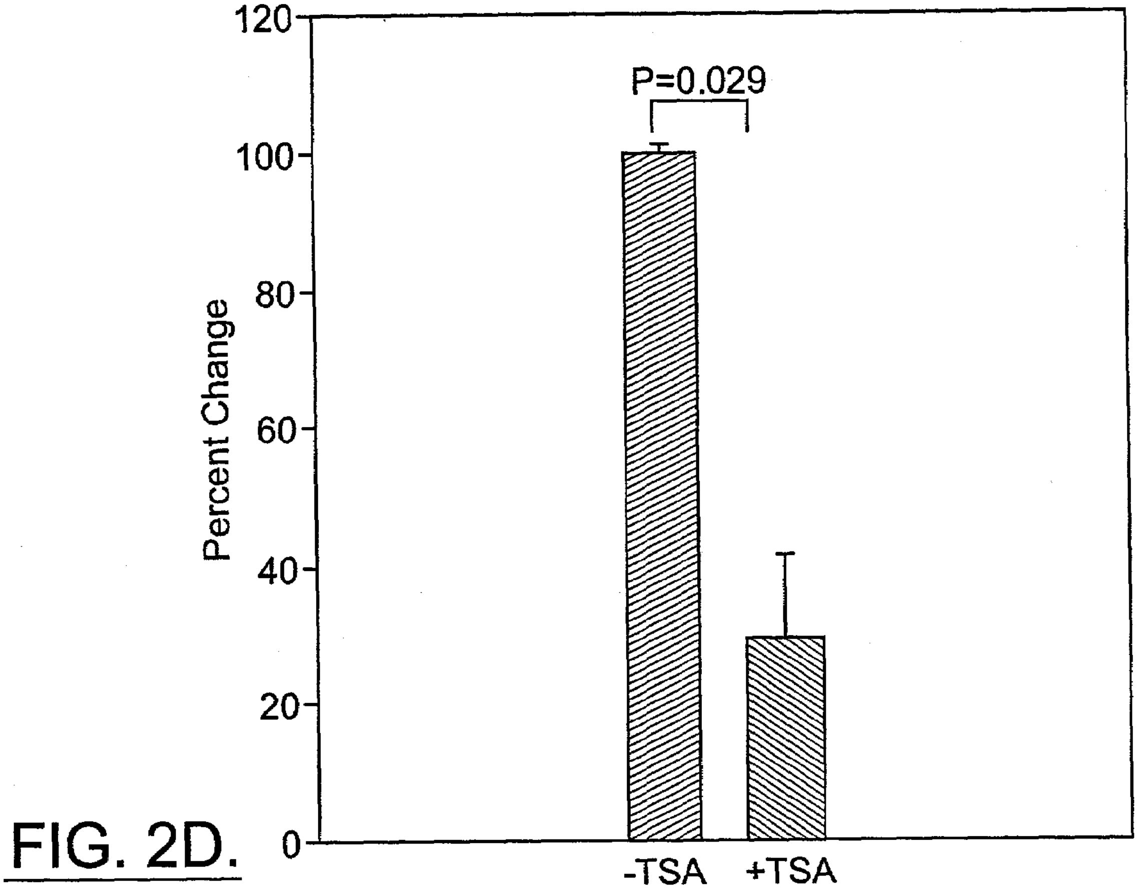
FIG. 2D shows a graphic depiction of a densitometric scan of the gel in FIG. 2C. This graph shows the percent change in IL-10 mRNA from SLE T cells cultured in the absence or presence of 1000 ng/ml TSA.
Figure 2E:
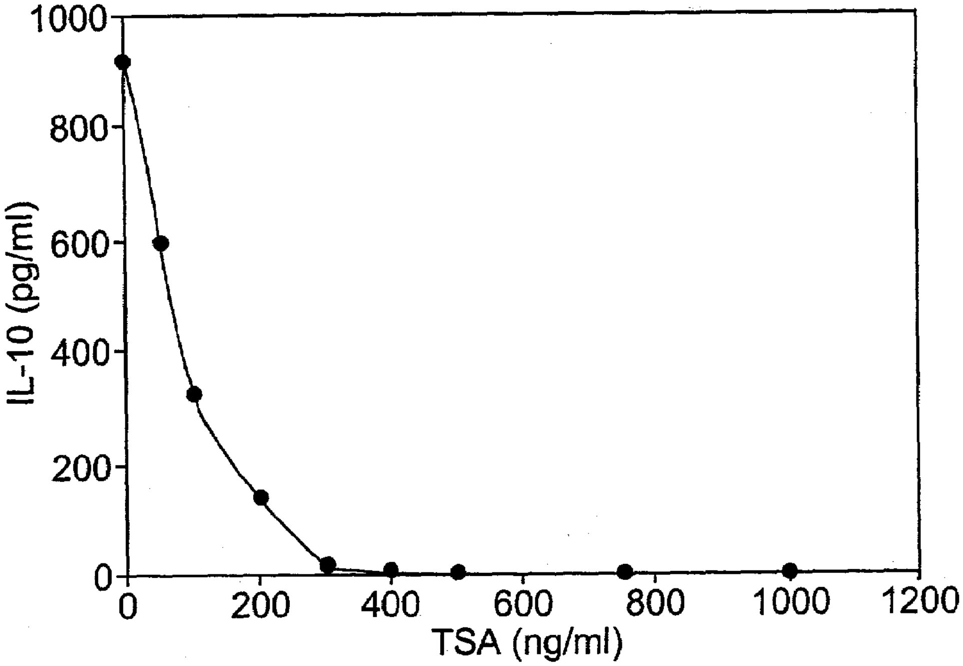
FIG. 2E illustrates the inhibition of IL-10 secretion by increasing concentrations of TSA over 24 hr.
Figure 2F:
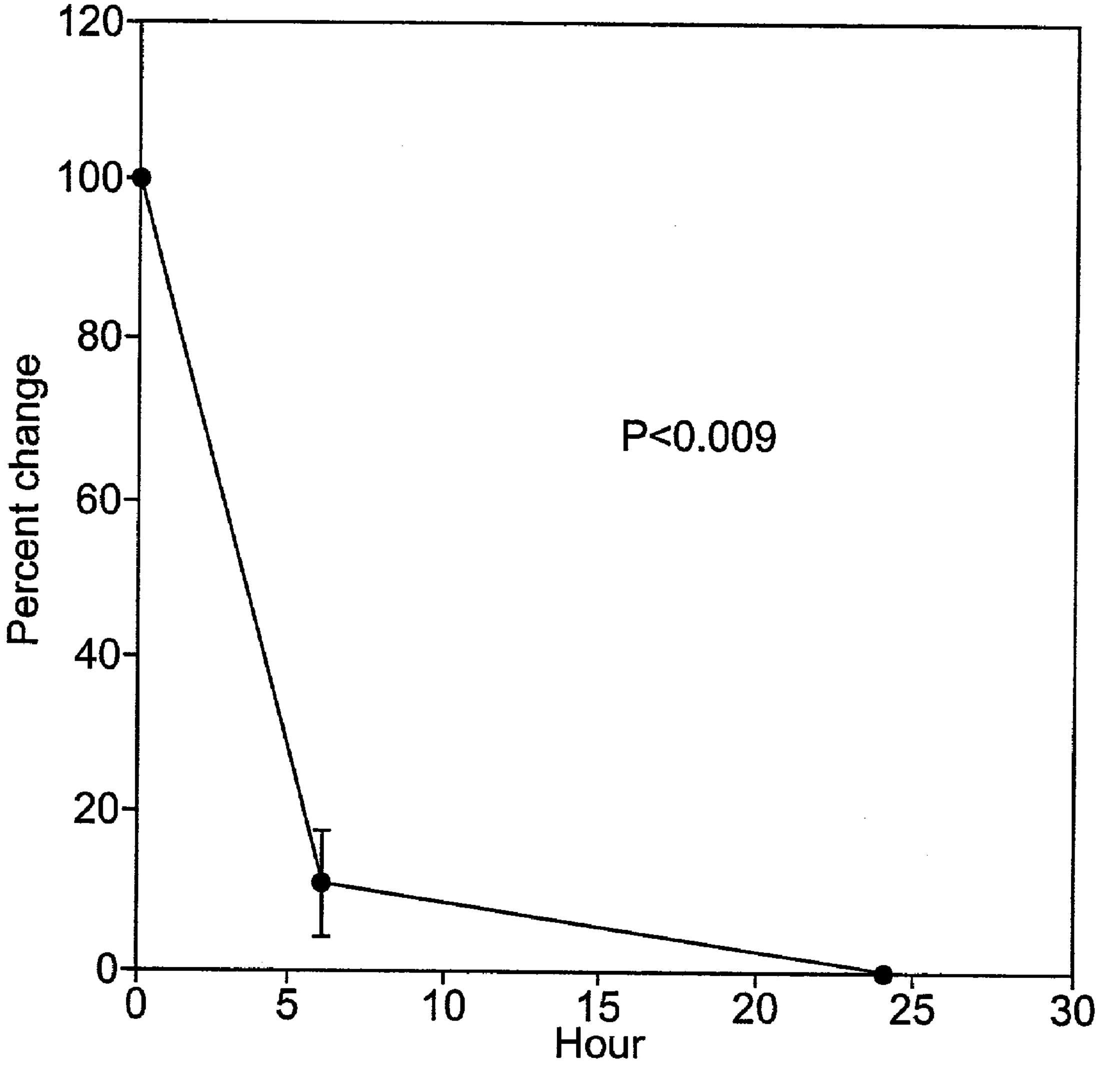
FIG. 2F depicts the percent change of IL-10 production over time. Statistical analysis was performed by paired Student's t test.

T cells from SLE subjects produce markedly increased amounts of IL-10 resulting in high serum levels of the cytokine (B. S. Handwerger, et al., in *Lupus: Molecular and Cellular Pathogenesis*, G. M. Kammer and G. C. Tsokos, Eds. (Humana Press, Totowa, N.J., 1999) chap. 21; E. Hagiwara, et al., *Arthritis Rheum.* 39, 379 (1996)). To determine whether TSA could down-regulate IL-10, a dose-response analysis was performed. Like CD154, increasing concentrations of TSA progressively inhibited IL-10 transcript expression (FIGS. 2A and 2B). In fact, based on sensitive reverse transcriptase-polymerase chain reaction (RT-PCR) analyses, no detectable IL-10 mRNA was identified at TSA concentrations of 700-800 ng/ml. By comparison, increasing concentrations of TSA did not modify GAPDH transcript expression (FIG. 2A and 2B). As shown in FIG. 2C, IL-10 transcripts were present in freshly isolated T cells (0 hr; lanes 1, 4, 7) and remained stable relative to GAPDH transcripts after culturing cells for 18 hr (lanes 2, 5, 8). However, when SLE T cells were cultured in the presence of TSA for 18 hr, no detectable IL-10 transcripts were identified (FIG. 2C, lanes 3, 6, 9). When IL-10 transcripts from all eight SLE subjects were quantified relative to GAPDH transcripts, TSA inhibited expression of IL-10 mRNA by 71% (FIG. 2D; P=0.029). Treatment of T cells from eight SLE subjects over 18 hr with increasing concentrations of TSA resulted in a dose-dependent inhibition of IL-10 protein production that was maximal at 300 ng/ml of the inhibitor (FIG. 2E). IL-10 and IFN-γ protein production were quantified by ELISA (R & D Systems, Minneapolis, Minn.). Within 6 hr, TSA inhibited IL-10 production by 90%; at 24 hr, there was complete inhibition of IL-10 synthesis (FIG. 2F). Thus, like CD154, TSA was able to block expression of IL-10 transcript, abolishing IL-10 production by SLE T cells.

EXAMPLE 3

Up-Regulation of IFN-γ Transcript and Protein Levels by TSA

Figure 3A:
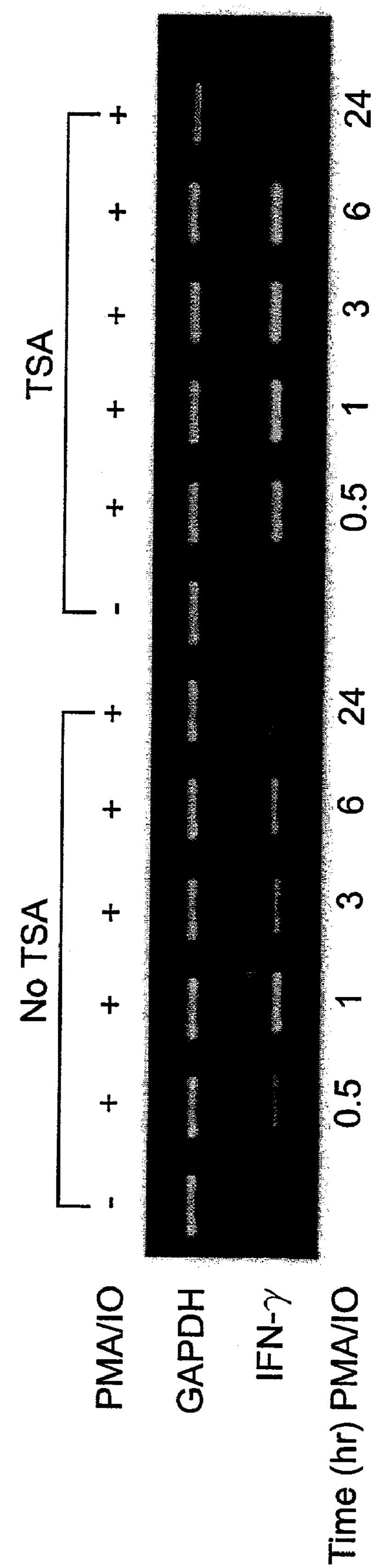
FIG. 3A shows the up-regulation of IFN-γ transcript by TSA. T cells were incubated in the absence or presence of 1000 ng/ml TSA over 18 hr. T cells were then stimulated with 20 ng/ml PMA+0.5 μM IO for intervals to 24 hr. IFN-γ mRNA expression relative to GAPDH mRNA expression is shown.
Figure 3B:
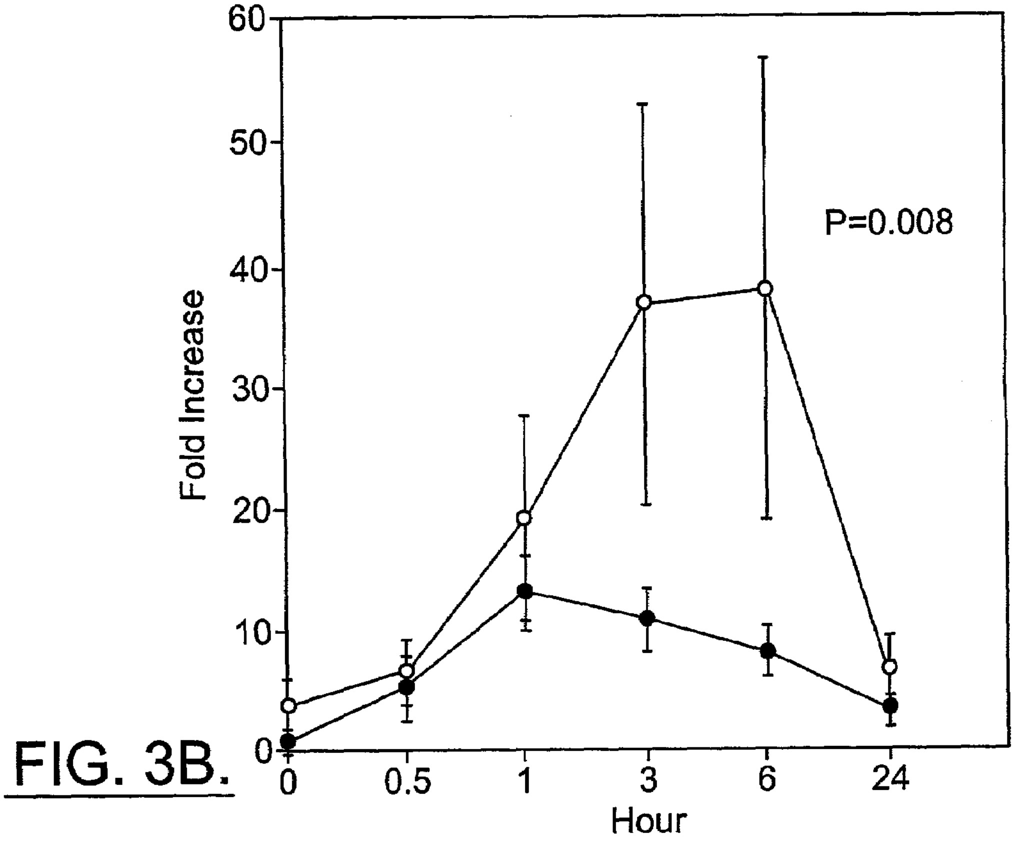
FIG. 3B demonstrates a graphic depiction of a densitometric scan of the gel in FIG. 3A. This graphs depicts the fold increase of IFN-γ mRNA in cells cultured in the absence (filled circles) or presence (open circles) of 1000 ng/ml TSA during intervals to 24 hr.

Low production of IFN-γ by SLE T cells may reflect down-regulation of gene expression (B. S. Handwerger, et al., in *Lupus: Molecular and Cellular Pathogenesis*, G. M. Kammer and G. C. Tsokos, Eds. (Humana Press, Totowa, N.J., 1999), chap. 21; E. Hagiwara, et al., *Arthritis Rheum.* 39, 379 (1996)). To establish whether TSA can up-regulate IFN-γ expression, SLE T cells were treated for 18 hr in the absence or presence of TSA. During that time, TSA induced a three-fold increase in IFN-γ transcript compared to untreated cells (FIG. 3A, lanes 1 and 7, and FIG. 3B). When T cells were activated with PMA+IO in the absence of TSA, peak IFN-γ transcript expression increased 13-fold at 1 hr over basal levels relative to GAPDH transcript, but waned thereafter. By contrast, activation of T cells in the presence of TSA induced a peak 37-fold increase in IFN-γ mRNA at 6 hr over untreated cells relative to GAPDH (FIGS. 3A and 3B; P=0.031). Thus, TSA up-regulated expression of IFN-γ transcripts in SLE T cells, yielding both a significantly increased and prolonged expression of the transcript.

Figure 3C:
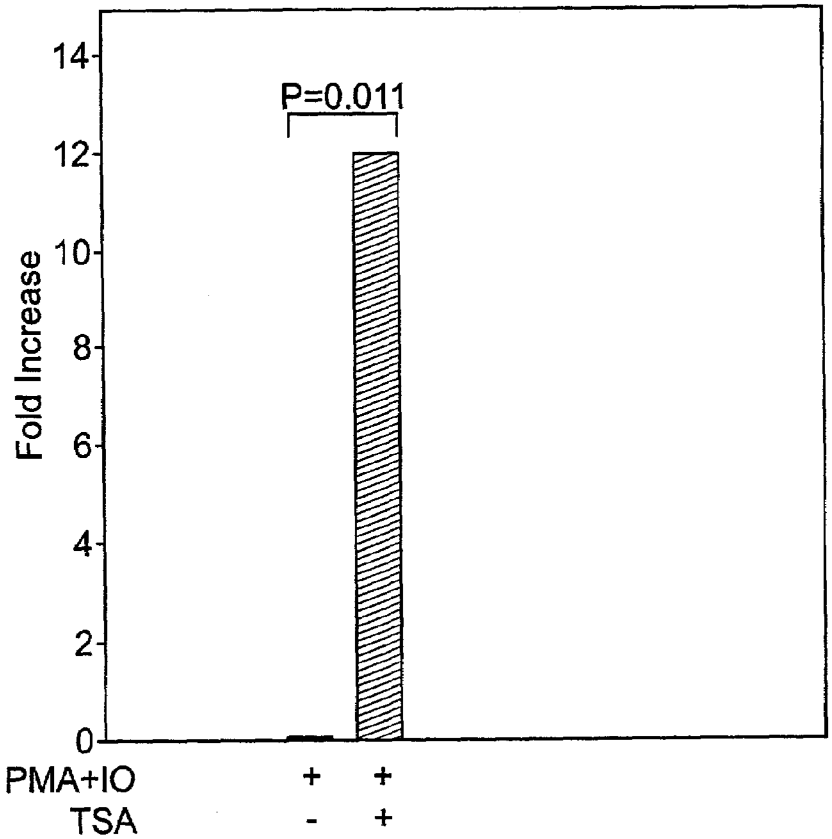
FIG. 3C illustrates IFN-γ protein levels from T cells cultured in the absence or presence of 1000 ng/ml TSA for 24 hr, and then stimulated with 20 ng/ml PMA+0.5 μM IO for 24 hr. The graph shows the fold increase of IFN-γ protein secretion. Statistical analyses were performed by paired Student's t test or one-way ANOVA.

This strong up-regulation of IFN-γ transcript was reflected in significantly increased production of IFN-γ protein by 24 hr. In the absence of stimulation, SLE T cells failed to produce any IFN-γ over 72 hr. When T cells were activated with PMA+IO for 24 hr, IFN-γ production increased about 24-fold. However, activation of T cells in the presence of TSA further enhanced IFN-γ output by >12-fold (P=0.011) (FIG. 3C). Taken together, these results demonstrate that TSA rapidly up-regulates both IFN-γ transcript and protein production by SLE T cells.

The capacity of TSA to down-regulate cell surface CD154 and IL-10 production and to up-regulate IFN-γ synthesis in SLE T cells provides new evidence in support of the proposition that skewed gene expression may be a fundamental mechanism underlying both the cellular and humoral immune dysregulation in this disease. That TSA was able to modify this altered gene expression in vitro also supports the concept that HDACs may be recruited to the promoter regions of these genes where they effect skewed expression.

Because the precise mechanism by which histone acetylation modifies transcription still remains uncertain (T. Kouzarides, *Curr. Opin. Genet. Dev.* 9, 40 (1999)), it is also unclear how inhibition of HDAC activity by TSA effects down-regulation of CD154 and IL-10 and up-regulation of IFN-γ in SLE T cells. Notwithstanding, this capacity of TSA to modulate the expression of these genes appears to have the salutary effect of normalizing their protein expression in vitro. Because it can simultaneously target multiple genes involved in the immunopathogenesis of lupus, TSA would be an effective therapeutic agent.

In SLE, a chronic inflammatory response progressively destroys organ parenchyma, ultimately leading to irreversible end-organ failure such as end-stage renal disease. The immunopathogenesis of this chronic inflammatory process is in part due to the presence of complement-fixing immune complexes. Formation of pathogenic immune complexes depends on production of autoantibodies, such as anti-native DNA, that arise from dysregulated B cell clones (B. H. Hahn, *New Engl. J. Med.* 338, 1359 (1998)). Therefore, down-regulation of CD154 and IL-10 should eliminate both the sustained CD154-CD40 interaction as well as high cytokine levels that drive polyclonal hypergammaglobulinemia and autoantibody production, reducing immune complex formation. Similarly, up-regulation of IFN-γ production might be expected to normalize an abnormal cellular immune response that predisposes to infections.

EXAMPLE 4

Up-Regulation of TGF-β1

Transforming growth factor β (TGF-β) derives from a family of pleiotropic cytokines that exhibit opposing biologic functions and is known to inhibit IL-1, IL-6 and TNF-β production by macrophages as well as IgG and IgM secretion by activated B cells in vitro. Kitamura et al., "Transforming growth factor-beta 1 is the predominant paracrine inhibitor of macrophage cytokine synthesis produced by glomerular mesangial cells", *J Immunol* 156:2964 (1996). Both constitutive and stimulated production of TGF-β by lymphocytes is significantly lower in SLE than controls. Ohtsuka et al., "Decreased production of TGF-beta by lymphocytes from patients with systemic lupus erythematosus" *J Immunol* 160:2539 (1998). This down-regulation of TGF-β may reflect the suppressive effects of high IL-10 levels on the cytokine's production by NK cells. Addition of TGF-β and IL-2 to SLE PBMCs almost completely abolishes the increased, spontaneous production of IgG by these cells and injection of TGF-β c-DNA into MRL/lpr mice decreases autoantibody production and prolongs their life-expectancy.

In contrast, the addition of anti-TGF-β mAb to SLE PBMCs resulted in increased spontaneous Ig synthesis, suggesting that decreased TGF-β leads to B cell hyperactivity. Del Giudice et al., "Role of transforming growth factor beta (TGF beta) in systemic autoimmunity", *Lupus* 2:213 (1993). This is further supported by the observation that TGF-β knockout mice reveal striking evidence of autoimmunity that resembles human SLE. Dang et al., "SLE-like autoantibodies and Sjogren's syndrome-like lymphoproliferation in TGF-beta knockout mice" *J Immunol* 155:3205 (1995). The sera of these mice contain elevated levels of predominantly IgG anti-dsDNA, -Sm and -ribonucleoprotein autoantibodies.

Figure 4:
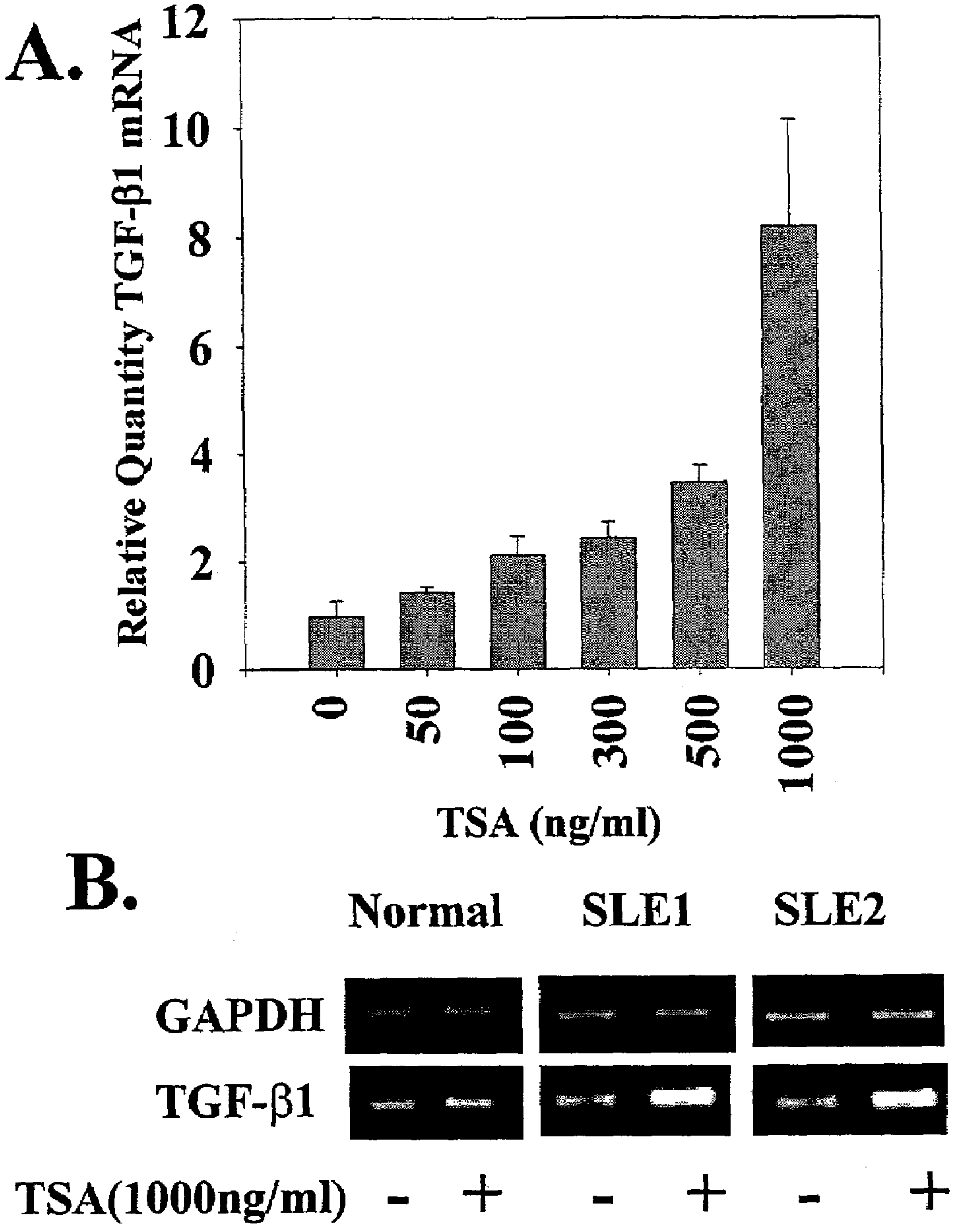
FIG. 4A is a bar graph showing that real time PCR was used to quantitate the amount of TGF-β1 mRNA relative to GAPDH mRNA in cells treated with increasing amounts of TSA.
FIG. 4B illustrates a comparison of the effect of TSA in normal vs. SLE patients.

Gene expression of TGF-β1 was tested to determine if the gene expression is suppressed by deacetylation of histones in SLE. In this determination, SLE PBMCs or isolated T cells were treated with the histone deacetylase inhibitors (HDIs), TSA or SAHA, for 18hr. As shown in FIG. 4A, concentrations of TSA to 500 ng/ml stimulated a modest increase in TGF-β1 mRNA, whereas 1000 ng/ml TSA resulted in an 8-fold induction of TGF-β1 mRNA in SLE T cells compared to vehicle treated cells. Subsequently, semi-quantitative PCR was performed to determine the amounts of TGF-γ1 transcripts in SLE and control T cells treated with vehicle or TSA (1000 ng/ml). FIG. 4B demonstrates that TSA increased TGF-β1 mRNA levels in SLE, but not in healthy control T cells. There is no change in GAPDH transcript in normal and SLE T cells after treatment of HDIs. Increased TGF-β1 transcript was associated with a subsequent increase in TGF-β1 protein secretion by SLE PBMCs. When compared to vehicle treated PBMCs, total TGF-β1 protein in culture supernatants from SLE PBMCs increased by approximately 30%. In contrast, there was no increase in total TGF-β1 secretion in TSA treated cells in normal healthy controls. Similar results may be obtained by SAHA.

Figure 5:
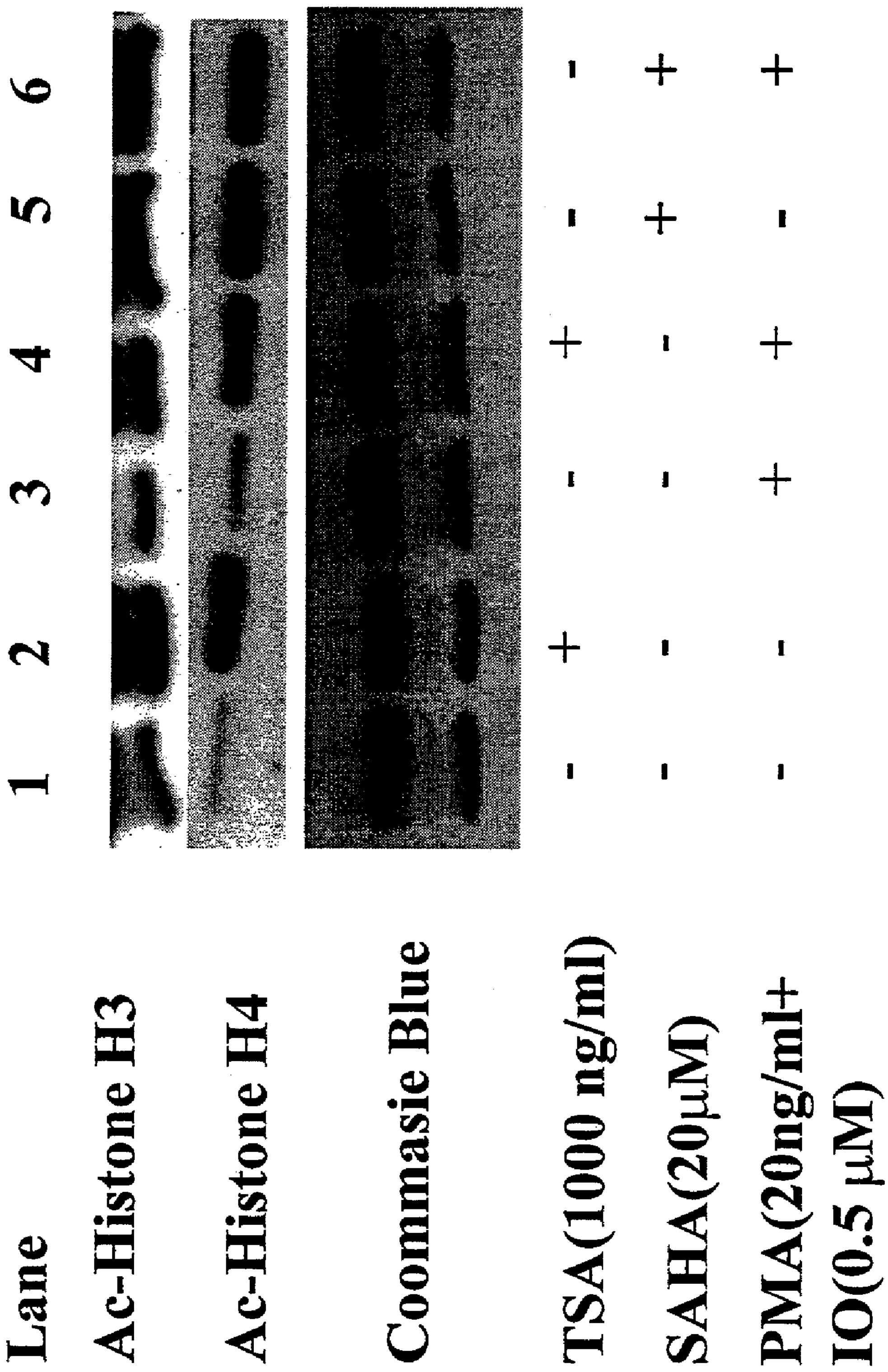
FIG. 5 depicts a Western blot analysis of acetylated histone H3 and H4 protein in SLE PBMCs treated with TSA or SAHA.

The effect of TSA and SAHA was examined to determine if HDIs induce accumulation of acetylated histones in SLE PBMCs on the level of histone acetylation in SLE PBMCs. Following culture of PBMCs in the presence of vehicle, 1000 ng/ml TSA or 20 μM SAHA for 18 hr, histones were isolated. Western immunoblot analysis showed that the level of acetylated H3 and H4 histones in vehicle-treated cells was low (FIG. 5, lane 1). By contrast, incubation with TSA or SAHA induced the accumulation of acetylated H3 and H4 histones (FIG. 5, compare lane 1 with 2 and 5). Stimulation of SLE PBMCs with PMA and Ionomycin alone did not result in increased accumulation of either acetylated histone H3 or H4 (FIG. 5, lane 3).

Figure 6:
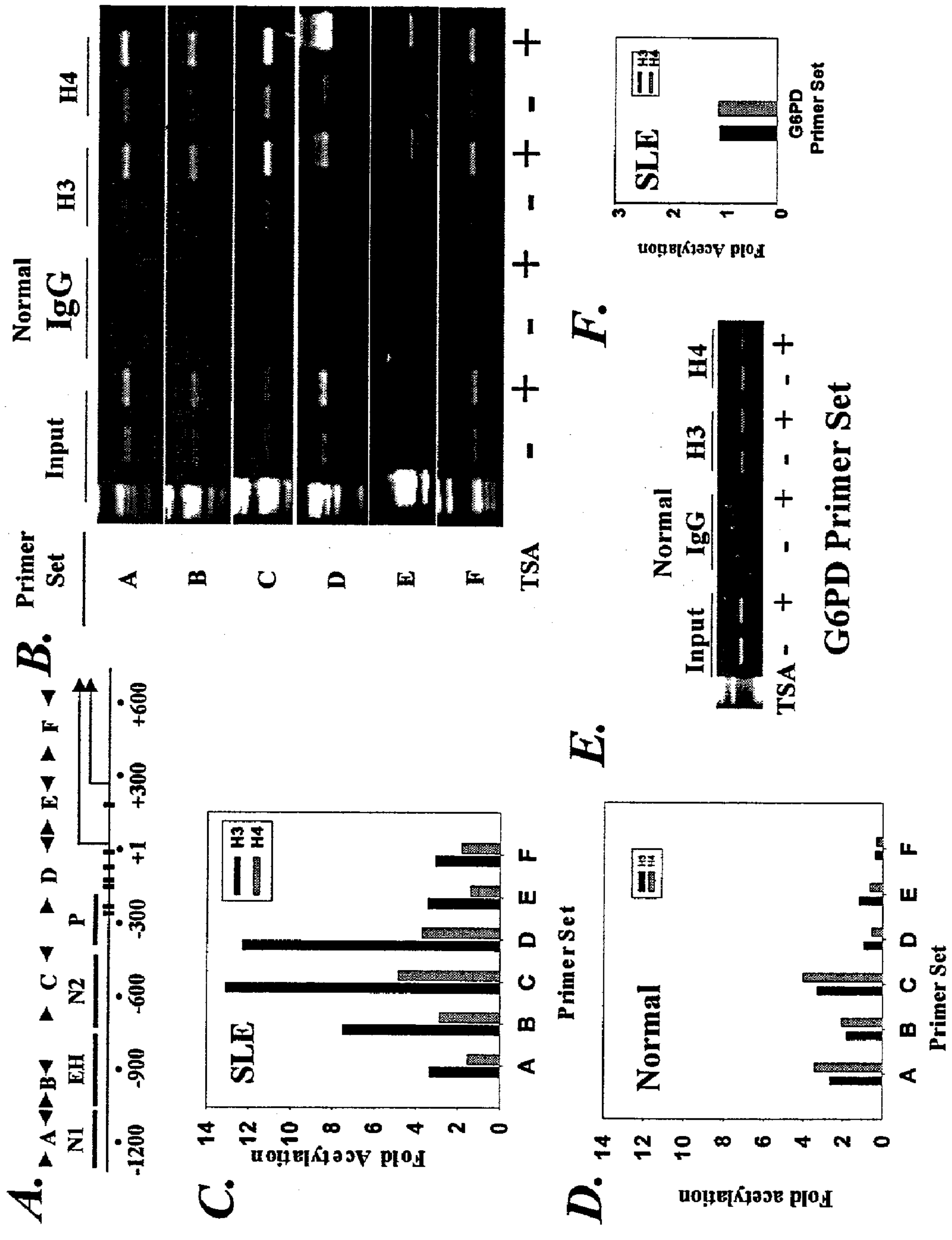
FIGS. 6A–6F demonstrate that TSA induces accumulation of acetylated H3 and H4 histones in chromatin associated with the TGF-β1 gene. Specifically.

The effect of HDAC inhibition on the acetylation of H3 or H4 associated with the TGF-β1 gene promoter was examined using the chromatin immunoprecipitation (ChIP) assay in an attempt to determine if HDIs induce accumulation of acetylated histones in chromatin associated with the TGF-β1 promoter in SLE PBMCs but not in healthy normal controls. The study undertaken included immunoprecipitating formaldehyde cross-linked, sonicated chromatin fragments from vehicle- and HDI-treated cells using anti-acetyl H3 and H4 antibodies, respectively. The immunoprecipitated DNA released from the bound protein was analyzed by quantitative PCR. A series of primer sets encompassing the TGF-β1 gene from −1.4 kbp to +0.6 kbp relative to the start site of transcription were created (FIG. 6A). Approximately a 12- and 4-fold enhancement of acetylated histones H3 and H4, respectively, in the TGF-β1 promoter in SLE was observed (FIGS. 6B & 6C). By contrast, essentially no enhancement of acetylated histones H3 and H4 at the TGF-β1 promoter in normal PBMCs treated with TSA was seen (FIG. 6D). The finding that silencing of the TGF-β1 gene is relieved by TSA may suggest that it is mediated by a mechanism leading to deacetylation of histones associated with its promoter in SLE PBMCs, but not in normal healthy controls.

To determine whether this effect was selective for the TGF-β1 gene in SLE PBMCs, the level of histone acetylation in the glucose-6-phosphate dehydrogenase (G6PD) gene was also examined. As shown in FIGS. 6E & 6F, there was no change in the levels of acetylated histones H3 and H4 at the G6PD gene in SLE PBMCs.

Figure 7:
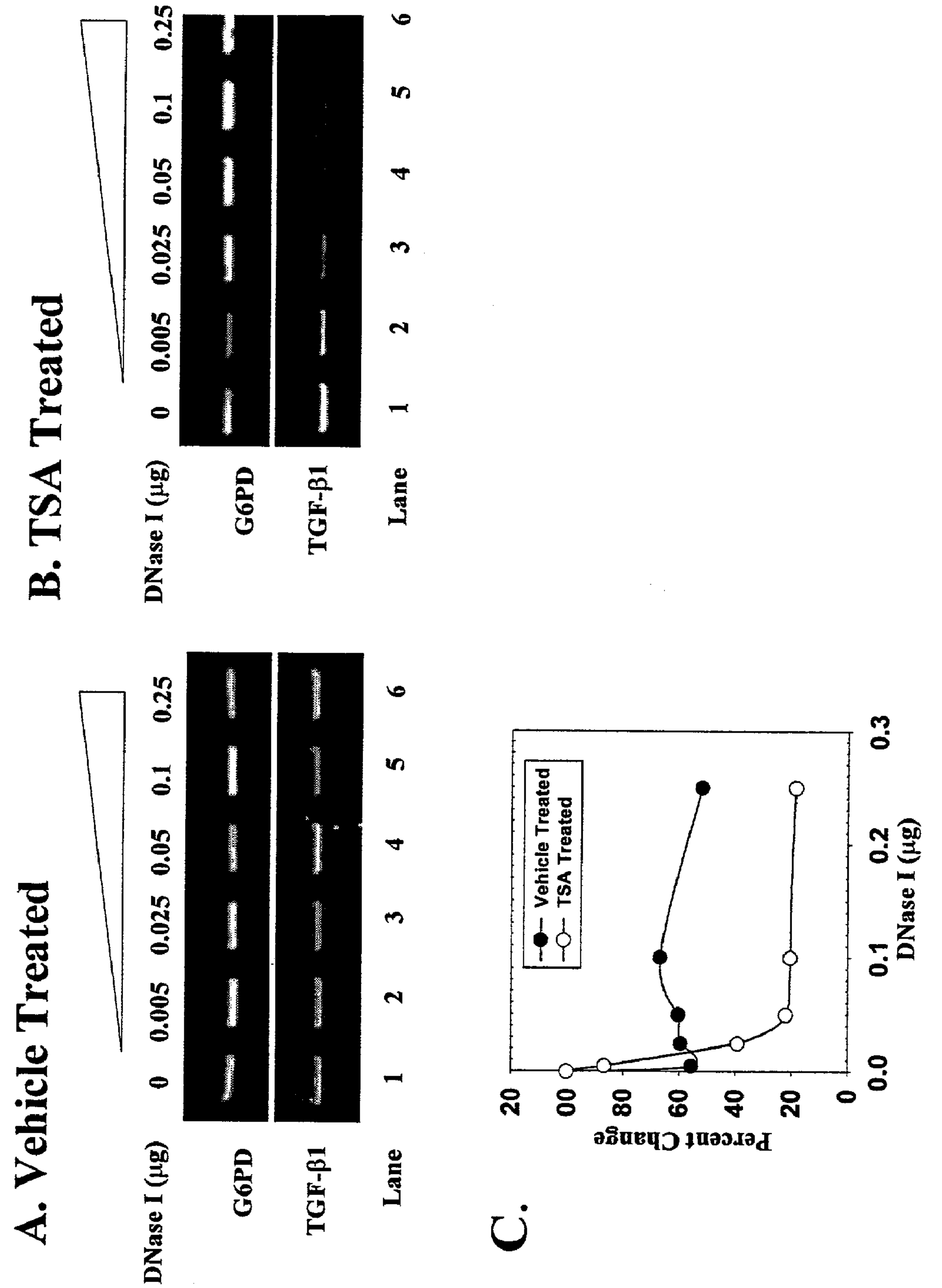
FIGS. 7A–7C depict Chromatin conformation of the TGF-β1 gene promoter analyzed by DNase I sensitivity assay.

Because acetylated histones are generally associated with transcriptionally active chromatin whereas deacetylated histones are often found in conjunction with an inactive chromatin state, a determination of whether HDAC inhibition could alter chromatin structure at the TGF-β1 gene locus was performed. Because nuclease susceptibility is one of the characteristics of active chromatin, a DNase I sensitivity assay was used to examine chromatin conformation of the TGF-β1 gene in SLE PBMCs in the absence or presence of TSA. SLE PBMCs were treated with 1000 ng/ml of TSA for 18 hr, a treatment course shown previously to result in an optimal increase of TGF-β1 mRNA. Equal amounts of purified nuclei isolated from vehicle- or TSA-treated cells were exposed to increasing concentrations of DNase I (FIGS. 7A & 7B). Changes in DNase sensitivity were measured by a DNase I-PCR assay using 0.5 μg of DNA. As shown in the FIG. 7A, the cells treated with only vehicle were relatively resistant to DNase I digestion, even with use of higher concentrations of DNase I (0.25 μg/μl). In contrast, cells treated with TSA were digested in the lower concentration (0.025 μg/μl) of DNase I (FIG. 7B; lanes 3-6). TSA treatment resulted in a three-fold increase in DNase I sensitivity (FIG. 7C), suggesting that inhibition of HDAC activity leads to a more open chromatin conformation in the TGF-β1 promoter of SLE PBMCs. There was no change in DNase I sensitivity at the G6PD gene promoter in vehicle- or TSA-treated SLE PBMCs (FIGS. 7A & 7B). Thus, it is likely that Trichostatin A increases DNase I sensitivity in the TGF-β1 gene of SLE PBMCs.

Additionally, because production of TGF-β1 by SLE lymphocytes is markedly impaired, (See, Ohtsuka et al., *J Immunol* 160, 2539-2545 (1998)), the hypothesis that HDAC may be associated with transcriptional repression of the TGF-β1 gene was tested and resulted in reduced TGF-β1 production. Exposure of SLE PBMCs to TSA and SAHA yielded an eight-fold increase in TGF-β1 transcript and a 30% rise in the synthesis of TGF-β1 protein. This enhanced transcriptional activation was temporally associated with increased acetylation of both H3 and H4 nucleosomal histones. Utilizing the ChIP assay, a twelve- and four-fold increase was demonstrated in acetylated H3 and H4 histones in the TGF-β1 promoter, respectively. The increase in total acetylated histones was not global; neither GAPDH nor G6PD genes were transcriptionally activated. Importantly, localized acetylation of the TGF-β1 promoter after treatment with TSA was not associated with a concomitant increase in SP1 binding. This suggests that TSA and SAHA modulate TGF-β1 promoter activity by a mechanism other than increasing the DNA binding capacity of SP1. Thus, the capacity of HDIs to increase the endogenous synthesis of TGF-β1 raises the possibility that these inhibitors could be therapeutic candidates for the treatment of SLE, atherosclerosis, and osteoporosis in addition to cancers.

EXAMPLE 5

Murine Models of SLE

Animal models provide a powerful tool to study disease mechanisms and to test novel therapeutic agents under well-defined conditions. Several mice model of lupus have been well characterized. The next few examples use MRL/lpr/lpr mice in their studies. The MRL/lpr/lpr mice closely resemble the human disease of SLE.

MRL/lpr/lpr Mouse Model of Lupus

Murphy and Roths developed the MRL/lpr strain and the congenic MRL/++ in 1976. They were derived from LG/J mice crossed with AKR/J, C3HDi, and C57BI/6. By the twelfth generation of inbreeding, MRL/lpr was derived. This mouse strain has a single spontaneous autosomal recessive gene mutation (lpr) of the fas apoptosis gene on chromosome 19. Interactions of Fas and Fas ligand (FasL) are required for the initiation of apoptosis in activated B and T lymphocytes under normal immunoregulatory conditions. Therefore, mice that are homozygous for the lpr mutation (i.e., lpr/lpr) develop massive lymphoproliferation, large quantities of IgG autoantibodies, and autoimmune disease.

Both male and female MRL/lpr mice develop high serum levels of immunoglobulins, monoclonal paraproteins, ANAs, and immune complexes at about 6 wks of age (4, 5). Males lag behind females by approximately 1 month. By 12-16 wks of age, there is serologic evidence of a panoply of autoantibodies IgM and IgG anti-ssDNA and anti-dsDNA and hypocomplementemia. Other autoantibodies in their repertoire include IgG antibodies that bind chromatin, histone, nucleosomes, nucleobindin (i.e., a DNA-binding protein), cardiolipin, erythrocyte surfaces, thyroglobulin, lymphocyte surfaces, Sm, U1 snRNP, Ro, La, Ku, Su, proteoglycans on endothelial cell membranes, neurons, ribosomal P, RNA polymerase I, Clq, and heat-shock proteins. A substantial portion develop IgG3 cryoglobulins, some containing rheumatoid factor activity. They develop clinical signs of arthritis, massive lymphadenopathy, skin disease, severe necrotizing arteritis, and glomerulonephritis (GN) by the age of 16-24 wks. Fifty percent of mice die from renal failure by 24 wk of age. Most MRL/lpr mice develop lymphocytic infiltration of salivary glands, pancreas, peripheral muscles and nerves, uvea, and thyroid. In fact, they develop clinical disease of hypothyroidism, abnormal electrical transmission in muscles and nerves (suggesting clinical polymyositis and polyneuritis), learning disabilities, sensorineural hearing loss, and band keratopathy. The thymus is structurally abnormal in MRL/lpr mice, as it is in all strains that develop spontaneous SLE. Thymic cortical atrophy is severe and medullary hyperplasia common. The numbers of epithelial cells in the subcapsular and medullary regions are decreased. Total cortical thymocytes are decreased in number. Thymectomy of newborn MRL/lpr mice prevents development of lymphoproliferation and autoimmune disease and MRL/lpr thymus engrafted into MRL/+/+ mice causes lymphoproliferation and early death from autoimmune nephritis.

Polyarthritis occurs in some MRL/lpr mice with prevalence between 15-25% . By 14 wks of age, there is synovial cell proliferation with early subchondral bone destruction and marginal erosion. Acute necrotizing arteritis, primarily of coronary and renal arteries, is found in over 50% of MRL/lpr mice. Many develop myocardial infarctions.

MRL/++ Mice

MRL/+/+ mice share over 95% of the genetic material of MRLlpr mice but differ at the 1 pr locus. MRL/+/+ mice are auto-immune prone and develop late-life lupus. They make anti-DNA, anti-Sm, and rheumatoid factors, but serum levels are lower than those of MRL/Ipr mice. Disease in MRL/+/+ mice does not show a gender bias, as male and females are similarly affected. Most mice develop clinical nephritis with advancing age.

C57B1/6J-lpr (B6/lpr/lpr) Mice (6)

B6/lpr/lpr mice do not develop arthritis, skin disease, glomerulonephrits or arteritis. They do not develop splenomegaly or lymphadenopathy until 8 months of age whereas MRL/lpr mice show lymphoid hyperplasia beginning at 4 months of age. B6/lpr/lpr mice have delayed 50% mortality (at 12 months) compared to MRL/lpr mice, which exhibit 50% mortality at 6 months of age.

EXAMPLE 6

Down-Regulation of Th1 and Th2 Cytokine Gene Expression

Figure 8:
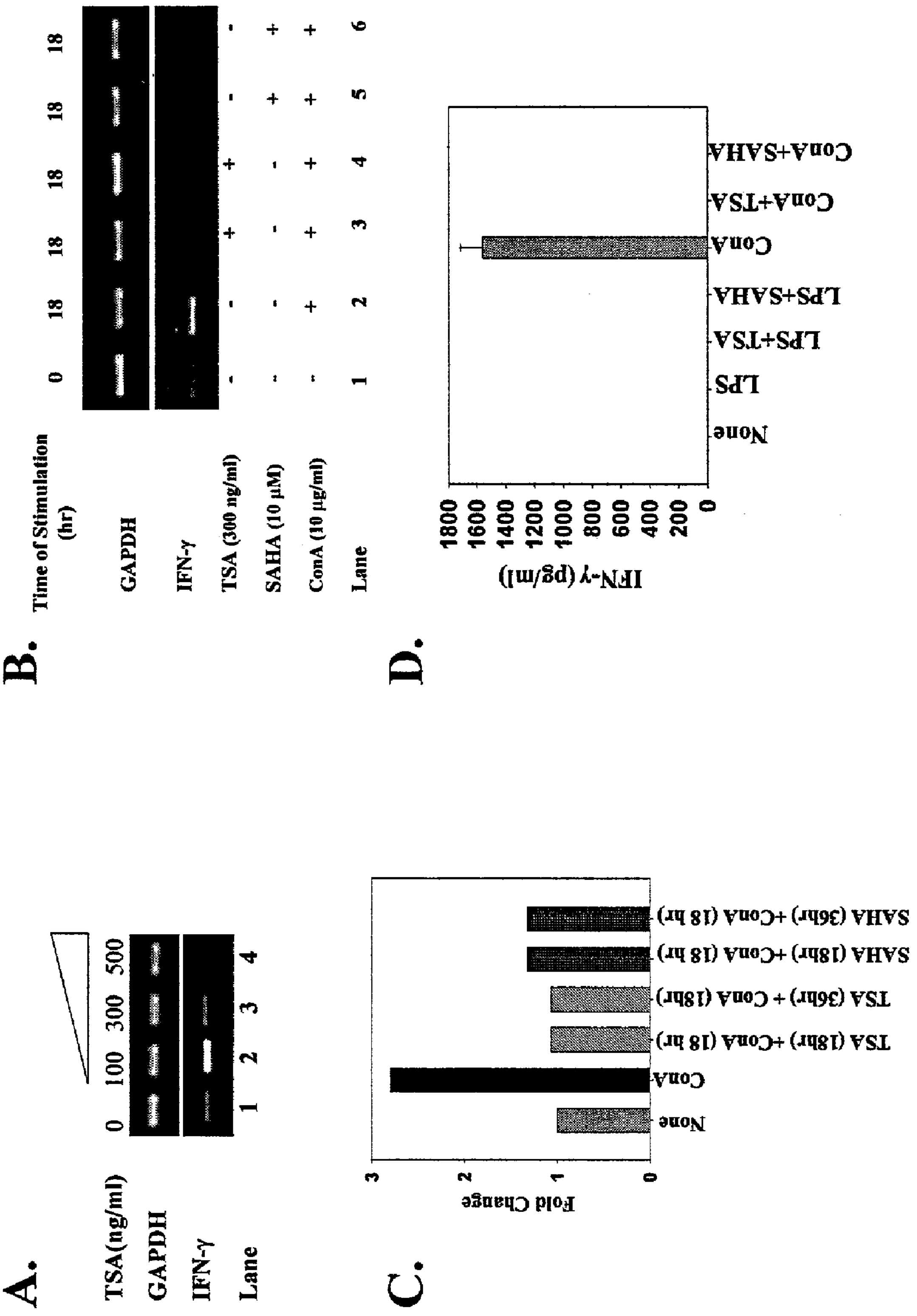
FIGS. 8A–8D illustrate that TSA and SAHA downregulate IFN-γ transcript and protein levels.

In determining whether TSA can down-regulate IFN-γ mRNA, splenocytes from older, 24-wk MRL/lpr mice were treated with 0 to 500 ng/ml of TSA for 18 hr. This interval was selected based on our data demonstrating optimal down-regulation of CD154 and IL-10 transcripts in human SLE T cells by TSA. Compared to splenocytes from 10-wk old mice that had low IFN-γ mRNA (FIG. 8B, lane 1), older mice had higher constitutive levels of IFN-γ transcripts normalized to the housekeeping gene, GAPDH (FIG. 8A, lane 1). Although low concentrations of TSA initially induced an increase in IFN-γ mRNA (FIG. 8A, lane 2), further increase in the concentration of TSA progressively inhibited IFN-γ mRNA (FIG. 8A, lanes 3 & 4). Maximal inhibition of IFN-γ transcript consistently occurred at 500 ng/ml of TSA. In contrast, expression of the housekeeping gene, GAPDH, remained stable. These results demonstrate that the heightened expression of IFN-γ mRNA in 24 wk old MRL/lpr splenocytes can be down-regulated by TSA.

To establish whether TSA or SAHA down-regulates Con A-induced IFN-γ mRNA expression, splenocytes from 10-wk old mice were stimulated with Con A (10 μg/ml) for 18 hr. From previous kinetic studies, IFN-γ mRNA is maximally expressed when T cells are activated for 18 hr. Con A stimulation consistently up-regulated IFN-γ mRNA content approximately 2.5-fold, but did not alter GAPDH mRNA expression (FIGS. 8B & 8C, lanes 1 vs. 2). In contrast, when splenocytes were preincubated with TSA or SAHA for 18 hr, up-regulation of IFN-γ transcript was markedly reduced compared with cells treated with the vehicle alone (FIGS. 8B & 8C, lanes 3–6). Dose titration experiments revealed that the optimal dose of SAHA was 10 μM (data not shown). Thus, both TSA and SAHA inhibit IFN-γ. mRNA up-regulation in response to mitogenic stimulation.

The marked inhibition of IFN-γ transcript by these inhibitors prompted us to quantify IFN-γ protein secretion in splenocyte culture supernatants. Over 72 hr, Con A, but not LPS, stimulated splenocytes from younger MRL/lpr mice to secrete a mean (±SEM) 1,563.2±88.3 pg/ml of IFN-γ (FIG. 8D). Con A-stimulated splenocytes cultured in the presence of either SAHA or TSA did not secrete detectable levels of IFN-γ protein (p=0.004, ANOVA FIG. 8D). Thus, inhibition of IFN-γ transcription by TSA and SAHA blocks secretion of IFN-γ protein by splenocytes.

Next, TSA and SAHA were tested to determine if they down-regulate expression of IL-12 p40 and IL-12 p35 mRNA, and IL-12 p40 protein. It is known in the art that IL-12 is a 75-kD cytokine comprised of a heterodimer with p35 and p40 subunits that are essential for the differentiation of the Th1 subset of $CD4^+$ T cells. However, at the level of transcription, each of these subunits is regulated independently. It promotes differentiation of $Th_1$, $CD4^+$ T cells. Administration of recombinant IL-12 (rIL-12) to younger MRL/lpr mice accelerates GN whereas anti-IL-12 mAb inhibits production of anti-dsDNA autoantibody in NZB/W $F_1$ mice.

Figure 9:
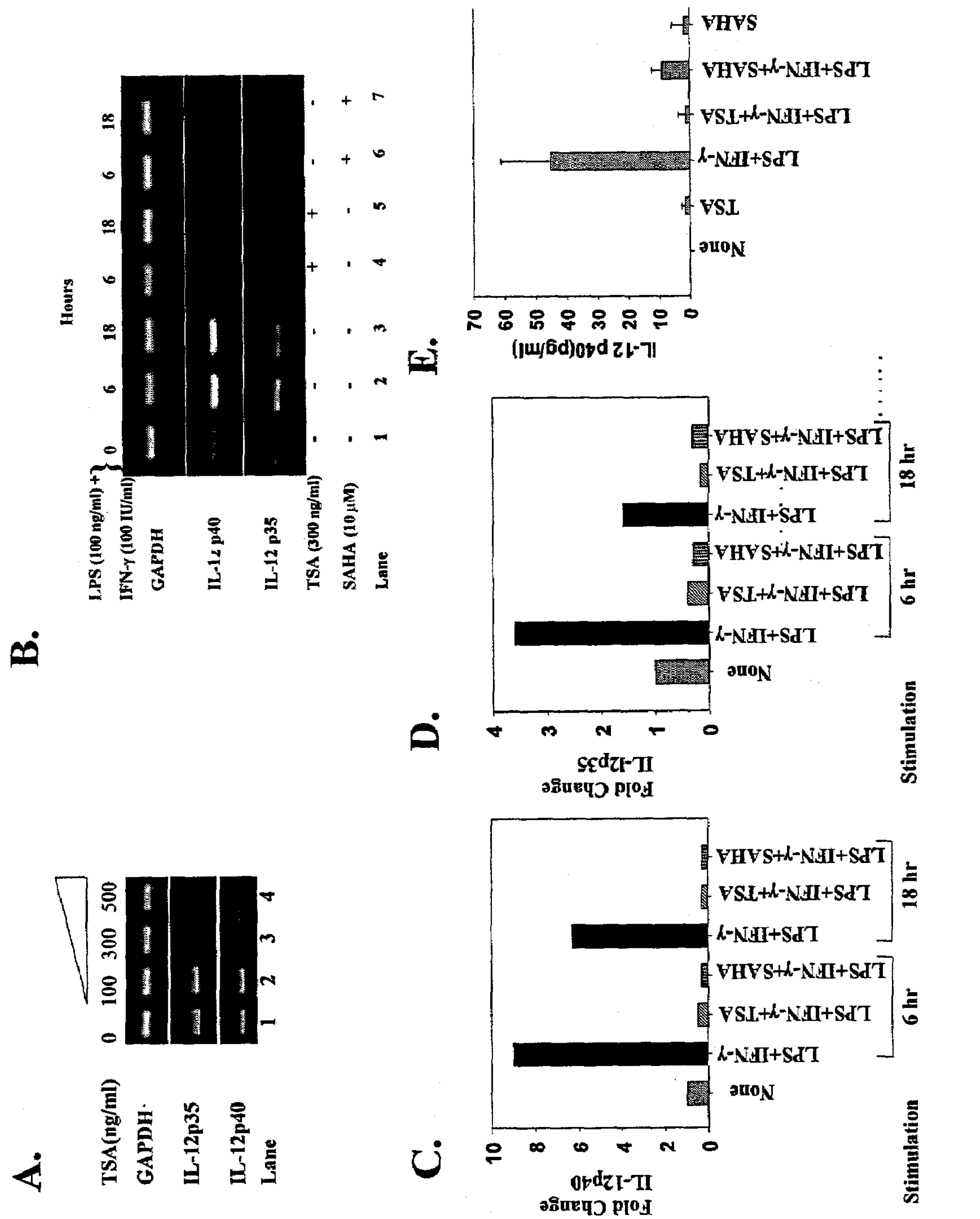
FIGS. 9A–9E demonstrate that TSA and SAHA downregulates IL-12 p35 and p40 transcript and IL-12 p40 protein levels.

In this study, the question of whether TSA down-regulates transcription of both IL-12 p35 and p40 subunit mRNA was investigated. Splenocytes from 24-wk MRL/lpr mice revealed constitutive expression of both IL-12 subunit transcripts (FIG. 9A). However, increasing concentrations of TSA above 100 ng/ml completely suppressed both transcripts (FIG. 9A, lanes 3&4). To address whether TSA and/or SAHA down-regulate LPS- and IFN-γ induced IL-12 p35 and p40 transcripts, splenocytes from 10-wk old MRL/lpr mice were incubated with vehicle, TSA or SAHA for 18 hr prior to stimulation. Splenocytes were stimulated with LPS and IFN-γ for 6 or 18 hr. FIGS. 9B-D demonstrate that, at 6 hr, there was a 9- and 3.5-fold increase of IL-12 p40 and p35 transcripts, respectively, when stimulated with LPS and IFN-γ following vehicle treatment; at 18 hr, the fold-increase was 6- and 1.5-fold for IL-12 p40 and p35 mRNA, respectively. When splenocytes were preincubated with TSA or SAHA for 18 hr and then stimulated with LPS and IFN-γ IL-12 p35 and p40 transcripts were undetectable (FIGS. 9B–D).

In the absence of stimulation, splenocytes did not secrete detectable IL-12 p40 after 24 hr in culture. When splenocytes were activated with LPS (100 μg/ml) and IFN-γ 100U/ml) for 24 hr the mean (±SEM) IL-12 p40 secretion was 45.3±9.1 pg/ml. However, stimulation of splenocytes in the presence of TSA or SAHA yielded significantly lower IL-12 p40 secretion after 24 hr (mean±SEM, TSA=1.5±1.4 pg/ml; SAHA 9.1±1.9 pg/ml; p=0.003 by ANOVA) (FIG. 9E). Taken together, these results may demonstrate that treatment with TSA and SAHA leads to decreased levels of IL-12 p35 and p40 transcripts and down-regulation of IL-12 p40 secretion by MRL/lpr splenocytes.

The present study also investigated whether TSA and SAHA down-regulate expression of IL-6 mRNA and protein. It is known in the art that IL-6 is also a Th2-derived proinflammatory cytokine that promotes B cell growth and differentiation. In SLE, there are increased numbers of circulating IL-6-producing cells that have increased levels of IL-6 transcript and intracellular IL-6 protein. In particular, IL-6 promotes MHC class II-restricted help of SLE T cell clones for autologous B cells, promoting production of both polyclonal and anti-self antibodies. High cytokine levels have been detected in cerebrospinal fluid and correlate clinically with central nervous system (CNS) involvement in lupus. Moreover, markedly increased amounts of IL-6 are secreted in the urine during lupus nephritis. High circulating levels of IL-6 have also been detected in the MRL/lpr murine model of SLE. Kiberd, "Interleukin-6 receptor blockage ameliorates murine lupus nephritis", J Am Soc Nephrol 4:58 (1993). Treatment of these mice as well as NZB/W mice with anti-IL-6 mAb diminishes anti-DNA autoantibody levels, delays the onset of proteinuria and significantly prolongs longevity. A diminution of anti-ds-DNA autoantibody production is also seen when human SLE B cells are treated with anti-IL-6 mAb in vitro.

Figure 10:
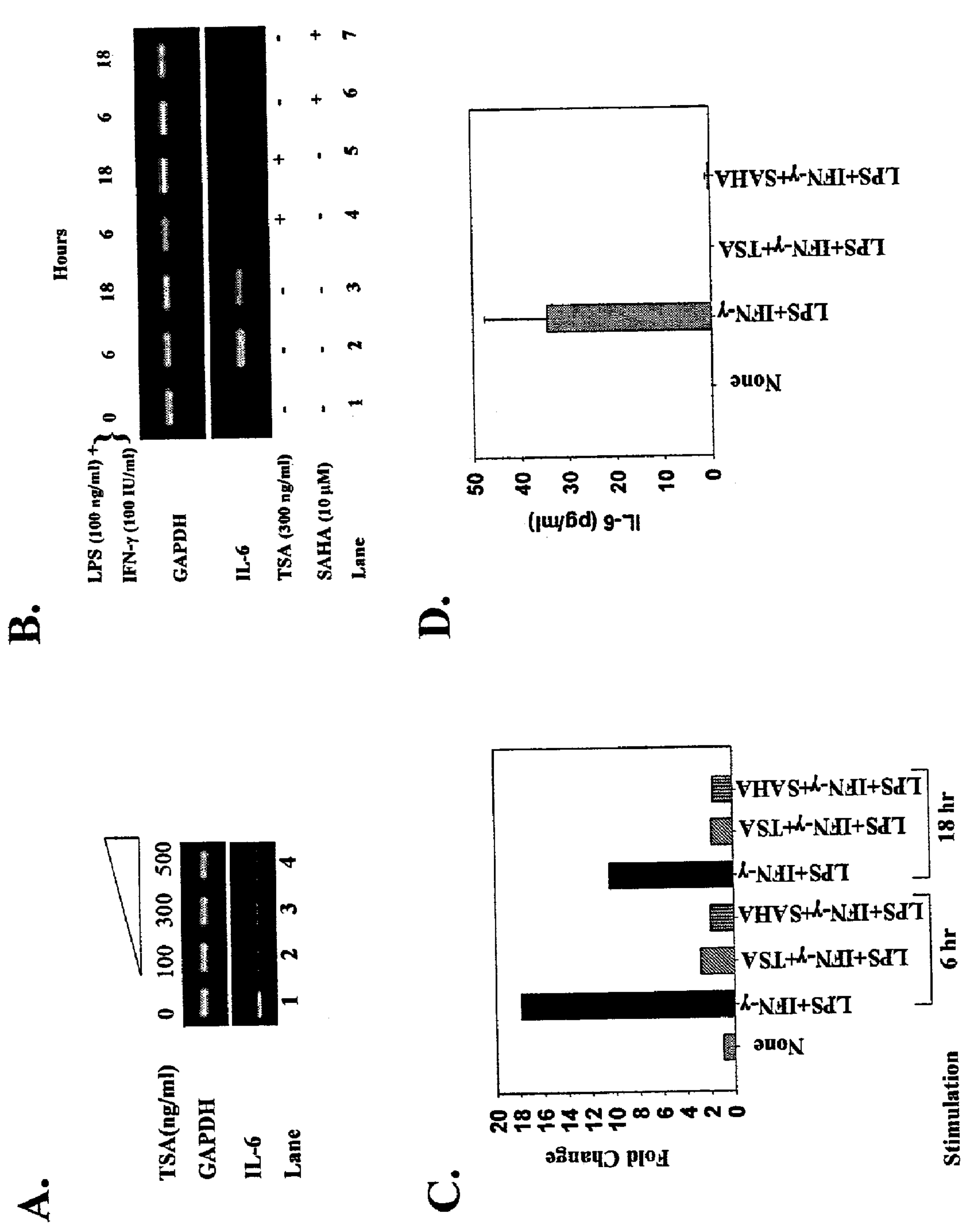
FIGS. 10A–10D show that TSA and SAHA downregulate IL-6 transcript and protein levels.

In determining whether TSA or SAHA down-regulate IL-6 mRNA content, splenocytes from 24-wk MRL/lpr mice were treated with increasing concentrations of TSA for 18 hr. In agreement with previous studies performed by the present application, significantly increased, constitutive IL-6 transcripts in 24-wk old mice (FIG. 10A, lane 1) were compared to 10-wk old mice (FIG. 10B, lane 1). As shown in FIG. 10A, TSA down-regulated IL-6 mRNA in a dose-dependent manner. TSA decreased IL-6 transcript at a concentration of 100 ng/ml and exerted maximal inhibition at 300 ng/ml. To address whether TSA and SAHA down-regulate LPS- and IFN-γ induced IL-6 transcript levels, splenocytes from younger MRL/lpr mice were treated in the absence or presence of TSA or SAHA for 18 hr before LPS and IFN-γ stimulation for 6 or 18 hr. As depicted in FIGS. 10B & 10C, IL-6 mRNA was up-regulated by LPS and IFN-γ stimulation 18-fold at 6 hr and 10-fold at 18 hr relative to GAPDH. In contrast, there was no detectable IL-6 mRNA in LPS- and IFN-γ stimulated splenocytes following pre-treatment with TSA or SAHA (FIG. 10B, lanes 4-7). Next, the effect of TSA and SAHA on IL-6 protein secretion in stimulated splenocytes was measured (FIG. 10D). When splenocytes were cultured with LPS and IFN-γ for 72 hr, there was a mean (±SEM) 34.4±7.6 pg/ml of IL-6 protein secretion. In contrast, treatment with TSA or SAHA in the presence of LPS and IFN-γ for 72 hr yielded no detectable IL-6 protein secretion (p=0.002, ANOVA FIG. 10D). Taken together, these results demonstrated that both TSA and SAHA down-regulated IL-6 mRNA and IL-6 secretion in MRL/lpr splenocytes.

TSA and SAHA Decrease Expression of IL-10 mRNA and Protein

IL-10 is a potent, Th2 growth and differentiation factor for activated B cells. Current evidence indicates that this cytokine plays a central role in autoantibody production. In vivo administration of rIL-10 accelerates autoimmunity whereas anti-IL-10 mAb delays the onset of anti-dsDNA autoantibody production, proteinuria, GN, and decreases mortality in NZB/W $F_1$ mice.

Figure 11:
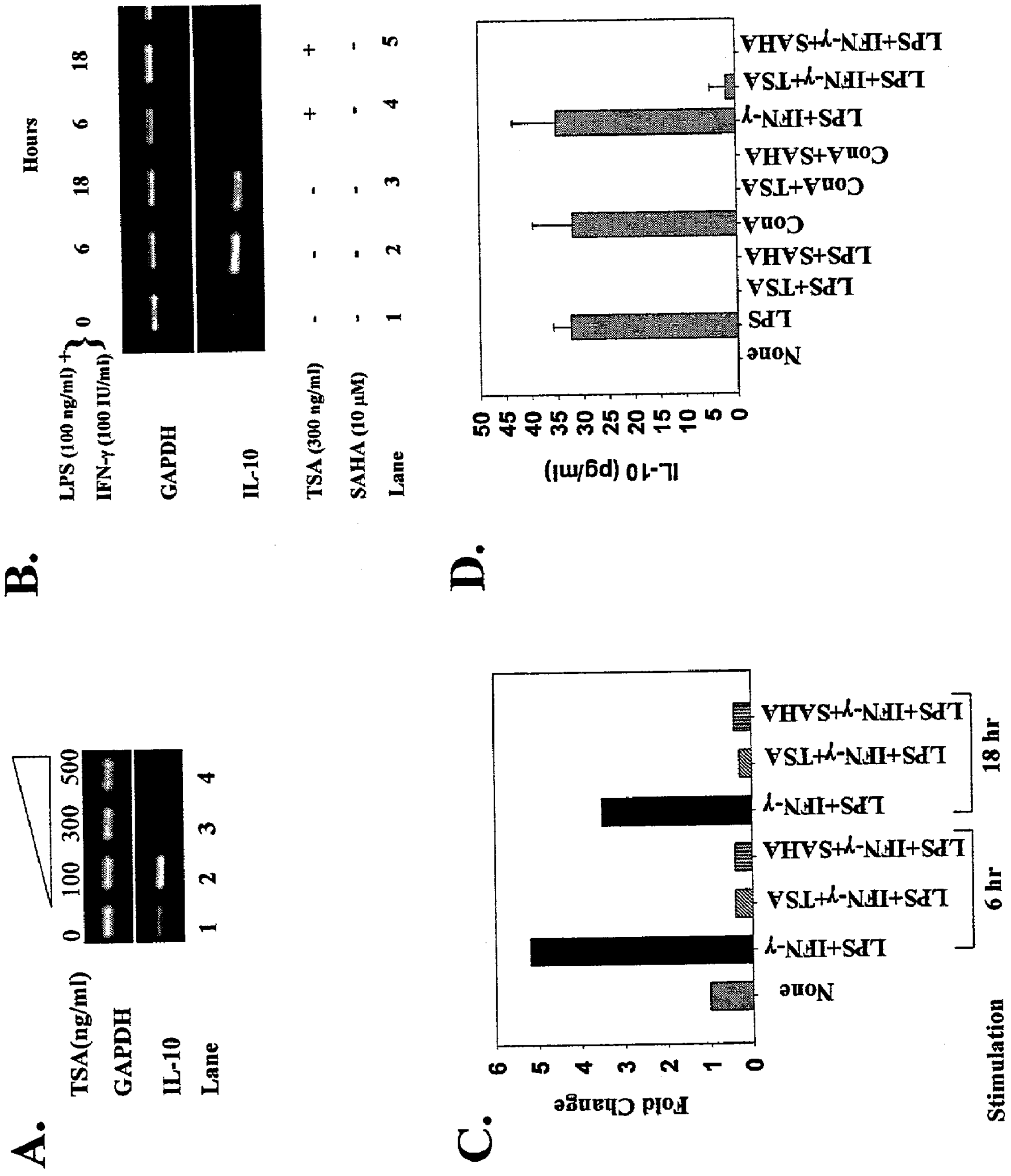
FIGS. 11A–11D show that TSA and SAHA downregulate IL-10 transcript and protein levels.

In investigating whether TSA down-regulates IL-10 mRNA, MRL/lpr splenocytes were treated with increasing concentrations of TSA. The heightened, constitutive expression of IL-10 mRNA confirms previous findings (FIGS. 11A & 11B, lane 1). TSA down-regulated IL-10 mRNA at a dose of 300 ng/ml. To address whether TSA and SAHA down-regulate LPS- and IFN-γ induced IL-10 transcript, splenocytes from 10-wk old MRL/lpr mice were treated in the absence or presence of TSA or SAHA for 18 hr before LPS and IFN-γ stimulation for 6 or 18 hr. FIGS. 11B & 11C demonstrate that IL-10 mRNA was up-regulated by LPS and IFN-γ stimulation approximately 5-fold at 6 hr and 3-fold at 18 hr relative to GAPDH transcript. There was no detectable IL-10 mRNA in TSA- or SAHA-pretreated splenocytes when stimulated with LPS and IFN-γ (FIG. 11B, lanes 4-7).

To determine the effect of TSA and SAHA on IL-10 protein secretion, MRL/lpr splenocytes were stimulated with Con A, LPS, or LPS+IFN-γ for 72 hr in the absence or presence of TSA or SAHA. As shown in the FIG. 11D, splenocytes stimulated with Con A, LPS, or LPS+IFN-γ secreted a mean (±SEM) of 31.8±4.5, 32.3±1.9, and 34.8±4.9 pg/ml, respectively, of IL-10 protein. When cells were pretreated with TSA or SAHA, there was no detectable IL-10 secretion when stimulated by either LPS, Con A, or LPS+IFN-γ (For SAHA: p<0.001, p=0.002, p=0.002, respectively; for TSA: p<0.001, p=0.002, p=0.003, respectively, ANOVA). Taken together, these results reveal that both TSA and SAHA down-regulate IL-10 mRNA levels and protein secretion.

TSA and SAHA Induce Accumulation of Acetylated Histones

Figure 12:
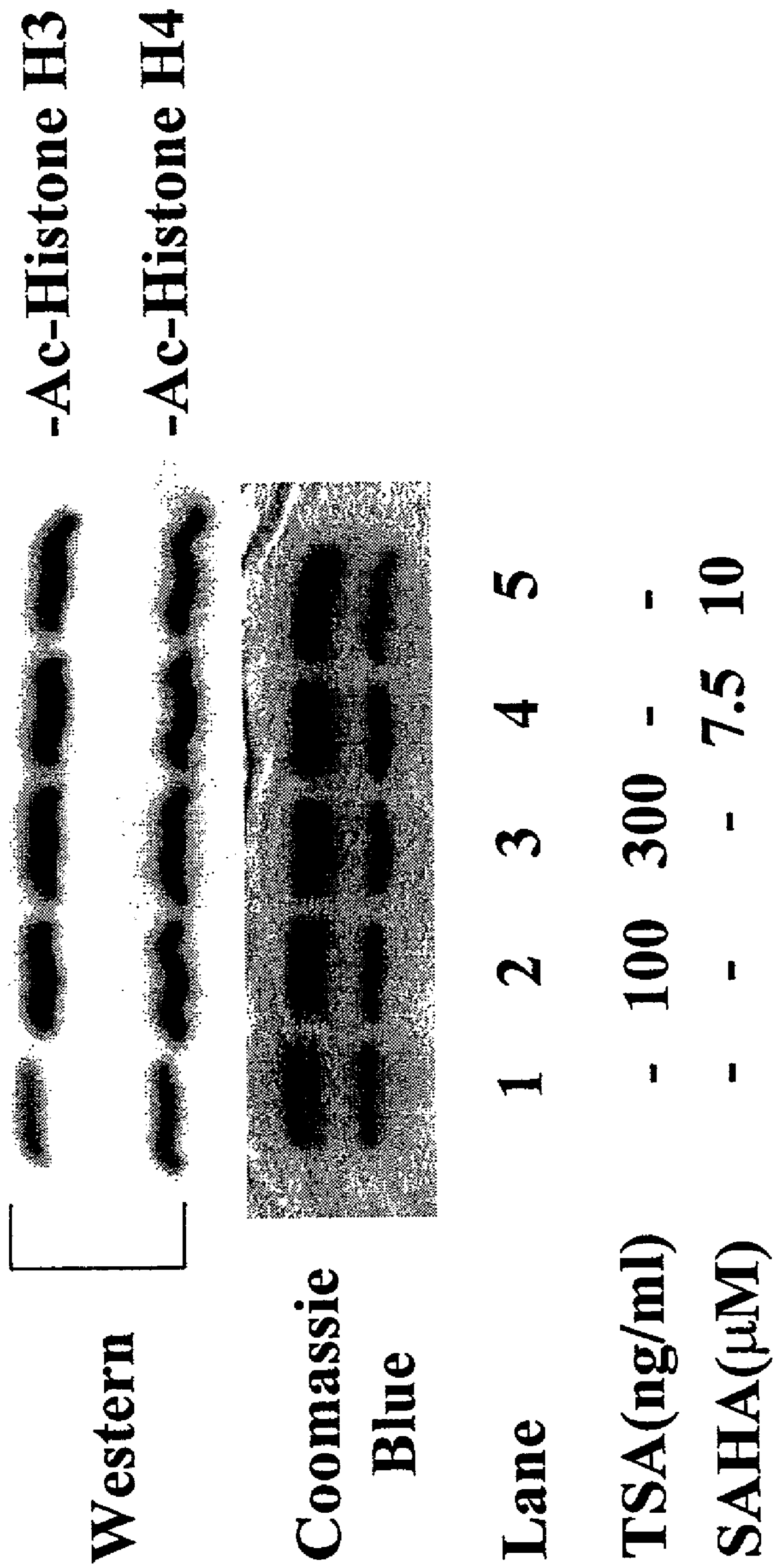
FIG. 12 illustrates a Western blot analysis of acetylated histone H3 and H4 protein in MRL/lpr splenocytes treated with TSA or SAHA.

One mechanism by which HDIs suppress transcription of cytokine genes in MRL/lpr splenocytes may be by increasing accumulation of acetylated histones which may result in chromatin remodeling. The accumulation of acetylated histones H3 and H4 in HDI-treated splenocytes was quantified to test this hypothesis. FIG. 12 is an immunoblot analysis of the acetylation levels of H3 and H4 histones. Following exposure of cells to TSA or SAHA for 18 hr, a marked increase in the accumulation of acetylated H3 and H4 histones was observed (compare Lanes 2-5 to Lane 1). These findings suggest that inhibition of HDAC by TSA and SAHA promotes acetylation of H3 and H4 histones, and supports the hypothesis that this mechanism may be involved in the down-regulation of several cytokine genes in MRL/lpr splenocytes.

Figure 13:
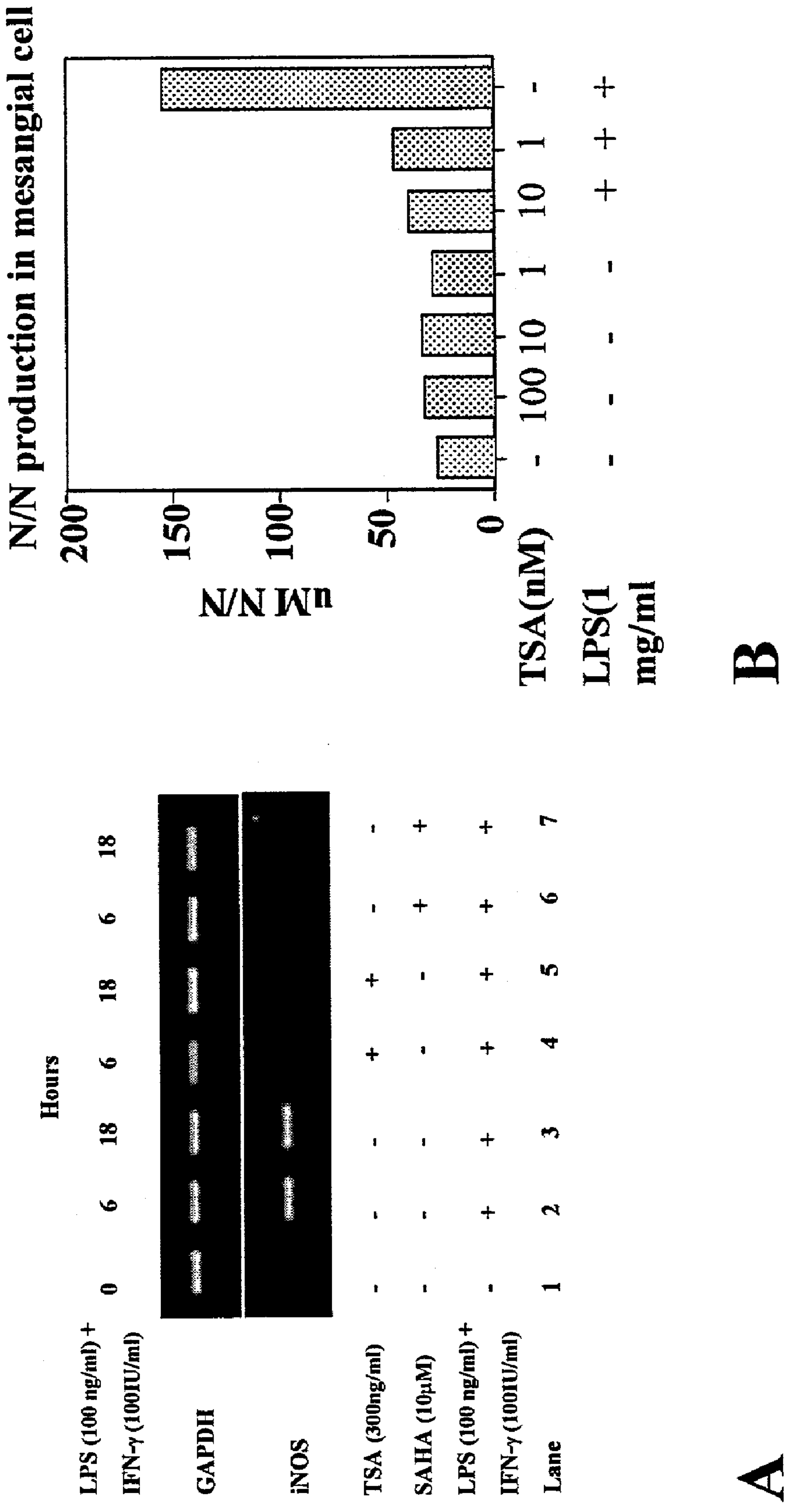
FIGS. 13A–13B examine whether histone deacetylase inhibitors could suppress inducible nitric oxide synthetase.

TSA and SAHA Decrease Inducible Nitric Oxide (iNOS) in Splenocytes and Nitric Oxide Secretion in Mesangial Cells Excessive production of nitric oxide (NO) is crucial to the initiation and maintenance of glomerulonephritis in MRL/lpr mice. Pharmacologic inhibition of NO synthesis in MRL/lpr mice abrogates disease progression. In examining whether HDIs could suppress inducible nitric oxide synthetase (iNOS), splenocytes from 10 wk old mice were stimulated in the presence or absence of TSA or SAHA with LPS and IFN-γ for 24 hr. Similar to Th1 and Th2 cytokines, these HDIs were able to suppress iNOS mRNA induction (FIG. 13A). To determine whether HDIs could suppress nitric oxide secretion by mesangial cells, mesangial cells were stimulated with LPS (1 mg/ml) in the presence of vehicle or TSA for 24 hr. The supernatant from the cell culture was assayed for nitric oxide. TSA was able to suppress LPS-induced nitric oxide production by mesangial cells (FIG. 13B).

EXAMPLE 7

In Vivo Study

Figure 14:
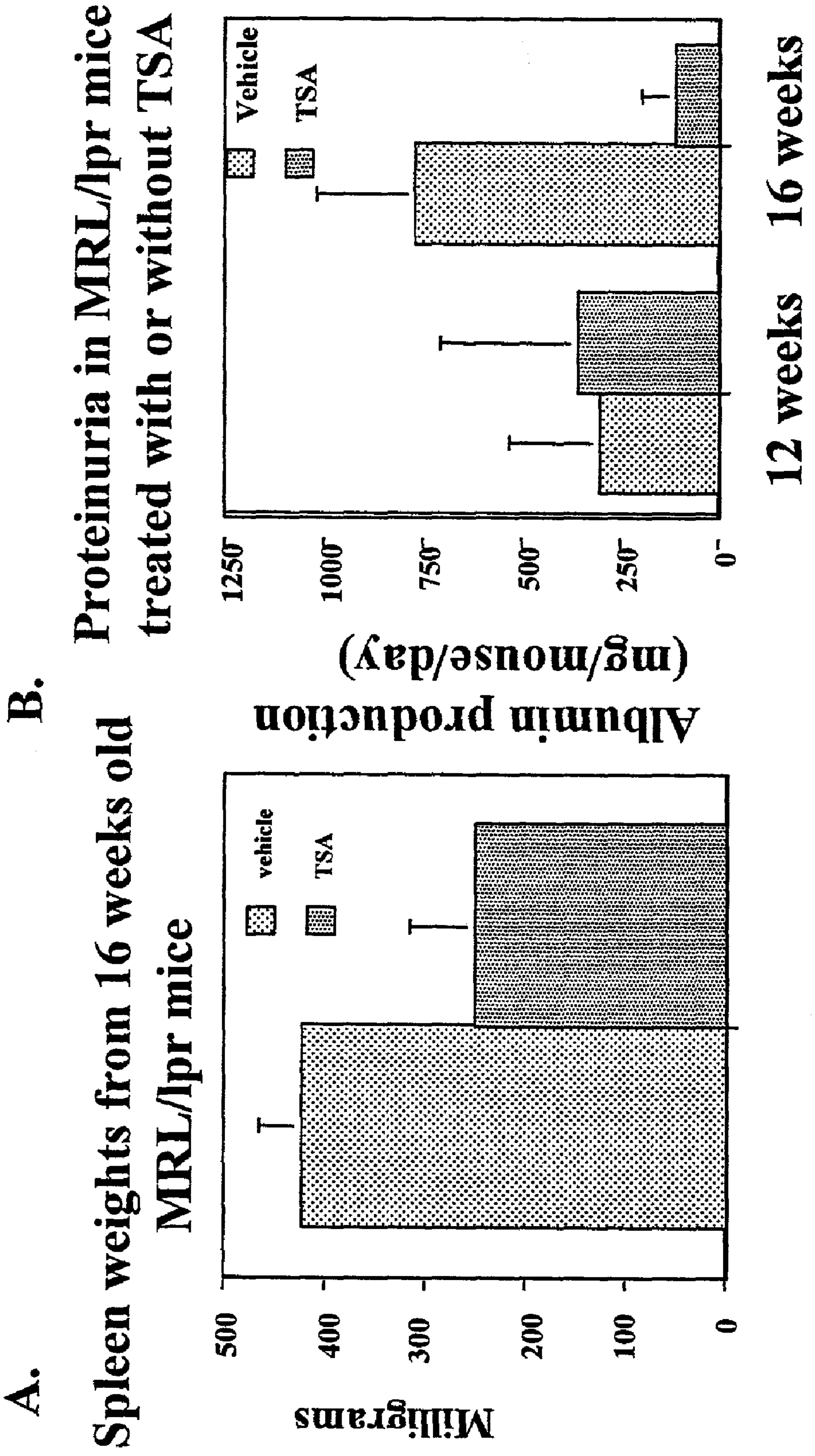
FIGS. 14A–14B are bar graphs illustrating the decrease in spleen weight (A) and proteinuria (B) in TSA.

In Vivo Administration of TSA Decreases Proteinuria, Lymphoproliferation, IFN-γ Secretion, and Physical Symptoms of Lupus in MRL/lpr Mice TSA was administered to MRL/lpr mice at 12 wks of age coinciding with the time of onset of clinical disease. TSA was given subcutaneously (sc) at a dose of 0.5 mg/kg dissolved in 40 μg DMSO; control mice were given the vehicle alone (40 μl DMSO). Proteinuria was assessed as a measure of albumin in mg/mouse/day prior to the initial dose (at 12 wks of age) and after four wks of treatment (at 16 wks of age). The results shown in FIG. 14B demonstrate that TSA prevented an increase in proteinuria observed in vehicle treated mice. After four weeks of treatment, nine mice in each group were sacrificed. At necropsy, the weight of the spleens were measured and sera was collected. The spleens were significantly decreased in weight in TSA treated mice compared to vehicle controls (FIG. 14A). This suggests that TSA prevents the lymphoproliferation and enlargement of spleens observed as disease progresses in MRL/lpr mice (as seen in vehicle treated mice). IFN-γ was measured by ellispot assay in splenocytes isolated from vehicle or TSA treated mice. There is a significant decrement in the number of IFN-γ secreting cells in TSA treated mice. In addition, the TSA treated mice showed signs of better overall health compared to vehicle controls.

In Vivo Administration of TSA Decreases Glomerulonephritis and Renal Score

Figure 15:
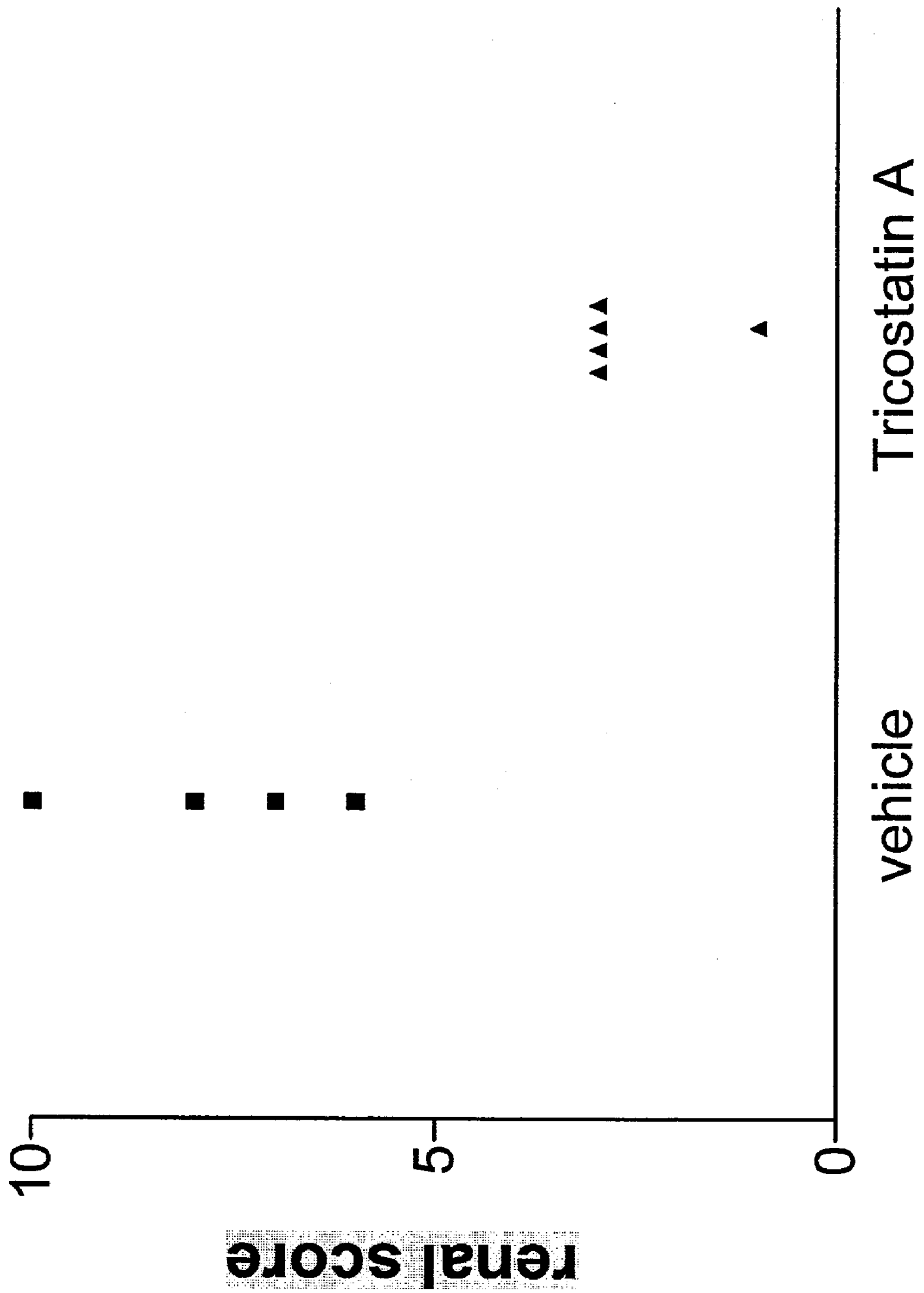
FIG. 15 is a graph showing the renal score for mice treated with vehicle or TSA.

TSA was administered to MRL/lpr mice at 12 wks of age at the time of onset of clinical disease. TSA was given subcutaneously (sc) at a dose of 0.5 mg/kg dissolved in 40 μl DMSO; control mice were given the vehicle alone (40 μl DMSO). After four weeks of treatment, nine mice in each group were sacrificed. One-half of one kidney was fixed in 10% formaldehyde/PBS, embedded in paraffin, and stained with hematoxylin and eosin. An examiner blinded to the treatment group quantified disease activity as follows: (a) Glomeruli were graded for hypercellularity (0-4), crescent formation (0-4), and inflammation (0-4). (b) The interstitium was graded for inflammation (0-4). Scores were additive (BALB/c mice historically receive scores of 0-0.5). Half of the second kidney was snap-frozen, embedded in OCT, frozen sections cut and analyzed for C3 deposition by immunofluorescence. TSA showed a significant reduction of glomerulonephritis and renal score (FIG. 15) after 4 weeks treatment, but did not show change in C3 deposition.

In vivo Administration of TSA Does Not Decrease Autoantibody Production

Figure 16:
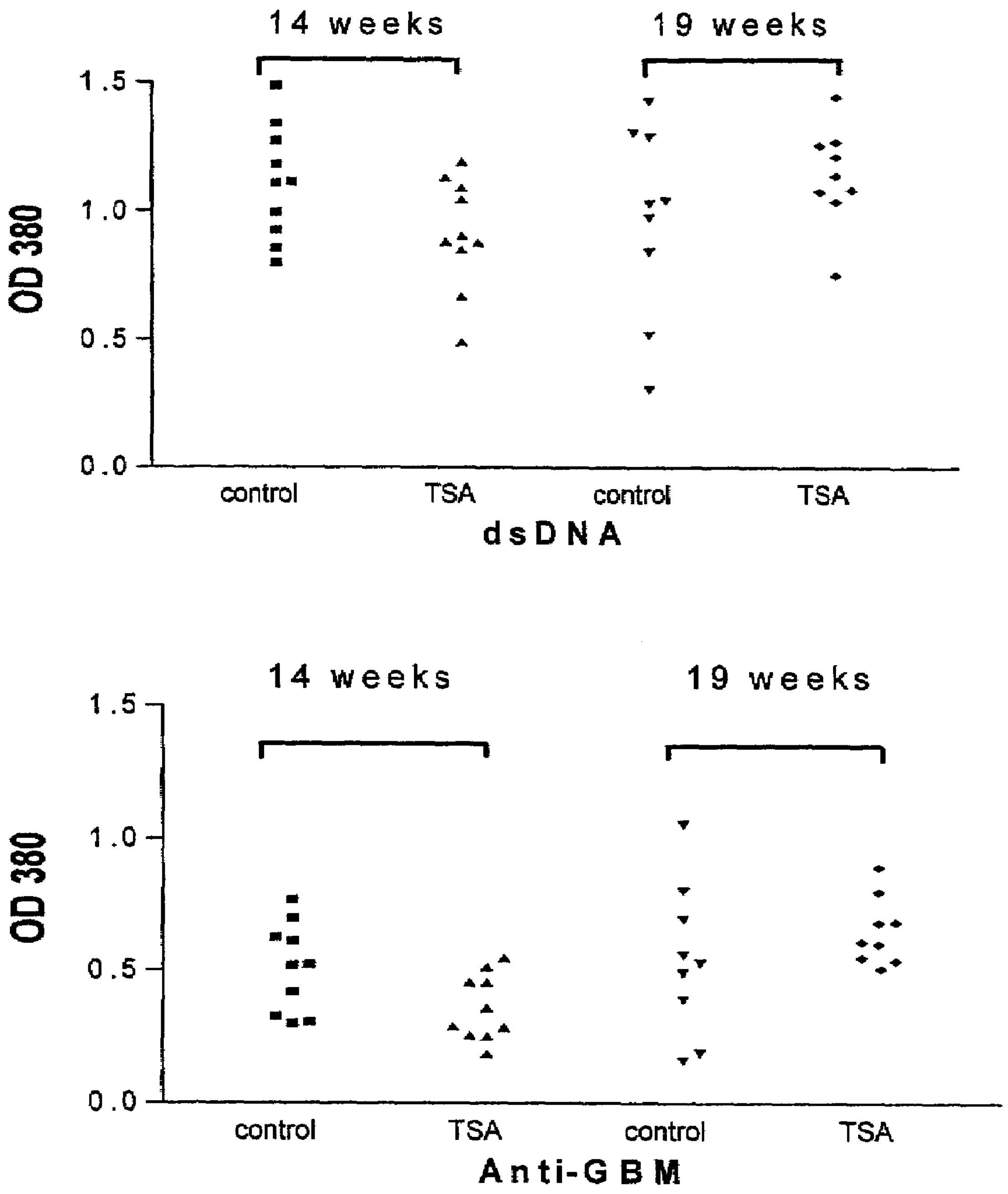
FIG. 16 shows two graphs demonstrating the autoantibody production in mice treated with vehicle or TSA where the sera levels of anti-dsDNA and anti-GBM were measured at 14 and 19 weeks of age, respectively.

In determining whether TSA suppresses autoantibody production anti-dsDNA and anti GBM-auto-antibodies were measured. There was no significant change between TSA or vehicle treated mice (FIG. 16). This result may indicate that TSA does not decrease anti-dsDNA levels in mice that have already developed the antibodies or this time point was too soon to see a positive effect (only 4 weeks treatment).

EXAMPLE 8

Suppression of Proteinuria and Nitric Oxide Secretion by HDIs in MRL/lpr/lpr Mice in Vivo The effect of TSA on proteinuria and nitric oxide secretion and increased survival in 26 week old MRL/lpr mice was examined. In this age group, MRL/lpr mice developed full-blown disease with evidence of proliferative immune-complex-mediated glomerulo-nephritis, vasculitis, arthritis, and massive lymphadenopathy. Most of the mice expired by the age of 30 weeks. Twelve 26 week old MRL/lpr mice were randomly selected to receive 5 mg/kg TSA in 50 ul DMSO or 50 ul DMSO as vehicle control by daily subcutaneous (s.c.) injection over the course of 4 weeks or until they exhibited distress. The data for the first two weeks is shown below. Urine was collected for a 24 hr time period on days 0, 7 and 14, and measured for protein and nitric oxide. Toxicity of TSA is being assessed by monitoring body weight, infection, abnormal behavior and survival of treated mice. In comparison to vehicle treated mice, six TSA treated mice have less proteinuria in day 7 and day 14 compared to day 0 (Table 1 and 2).

TABLE 1

| Proteinuria (ug/day) in vehicle treated mice | | | |
|---|---|---|---|
| MOUSE | DAY 0 | DAY 7 | DAY 14 |
| 1 | 41.2 | 32.7 | 40.1 |
| 2 | 8.1 | 4.27 | 3.15 |
| 3 | 2145 | 1869 | 3511 |
| 4 | 69.5 | 34.9 | 65.1 |
| 5 | 533 | 47 | 685 |
| 6 | 12.6 | 4.01 | 4.76 |

TABLE 2

| Proteinuria (ug/day) in TSA treated mice. | | | |
|---|---|---|---|
| MOUSE | DAY 0 | DAY 7 | DAY 14 |
| 1 | 16689 | 274 | 865 |
| 2 | 213 | 54 | 82 |
| 3 | 14420 | 4701 | 3081 |
| 4 | 107 | 80 | 25 |
| 5 | 5 | 9 | 10 |
| 6 | 964 | 340 | 242 |
| 7 | 10 | 4.6 | 4.3 |

The foregoing is illustrative of the present invention, and is not to be construed as limiting thereof. The invention is defined by the following claims, with equivalents of the claims to be included therein.

What is claimed is:

1. A method of treating an autoimmune disease selected from the group consisting of rheumatoid arthritis, Siogren's syndrome, and uveitis in a subject in need thereof, comprising:

administering to said subject a therapeutically effective amount of a histone hyperacetylating agent selected from the group consisting of Trichostatin A and Trichostatin C, or a pharmaceutically acceptable salt thereof.

2. A method of treating systemic lupus erythematosus in a subject in need thereof, comprising administering to said subject a therapeutically effective amount of a histone hyperacetylating agent selected from the group consisting of Trichostatin A and Trichostatin C, or a pharmaceutically acceptable salt thereof.

3. A method of treating an autoimmune disease selected from the group consisting of rheumatoid arthritis, Siogren's syndrome, and uveitis in a subject in need thereof, the method comprising:

administering to said a subject a histone hyperacetylating agent in an amount effective to treat the disease, wherein said histone hyperacetylating agent is selected from the group consisting of Trichostatin A and Trichostatin C, and wherein the agent binds to a histone in vivo.

4. A method according to claim 3, wherein the agent is administered in a pharmaceutical composition which includes a pharmaceutically acceptable carrier or diluent.

5. A method of treating an autoimmune disease selected from the group consisting of rheumatoid arthritis, Siogren's syndrome, and uveitis, in a subject in need thereof, the method comprising:

administering to the subject a pharmaceutical formulation comprising a pharmaceutically acceptable carrier and a compound selected from the group consisting of trichostatin A and trichostatin C, or a pharmaceutically acceptable salt thereof, in an amount sufficient to treat a symptom of the autoimmune disease.

6. A method of treating systemic lupus erythematosus and cutaneous lupus erythematosus in a subject in need thereof, comprising administering to said subject a therapeutically effective amount of a histone deacetylase inhibitor selected from the group consisting of Trichostatin A and Trichostatin C, or a pharmaceutically acceptable salt thereof.

* * * * *

UNITED STATES PATENT AND TRADEMARK OFFICE

CERTIFICATE OF CORRECTION

PATENT NO. : 7,271,198 B2 
APPLICATION NO. : 10/151481
DATED : September 18, 2007
INVENTOR(S) : Kammer et al.

It is certified that error appears in the above-identified patent and that said Letters Patent is hereby corrected as shown below:

Column 3, Line 39: Please correct “µMIO”
To read -- µM IO --

In The Claims:

Column 27, Claim 1, Line 3: Please correct “Siogren’s”
To read -- Sjogren’s --

Column 27, Claim 3, Line 18: Please correct “Siogren’s”
To read -- Sjogren’s --

Column 28, Claim 5, Line 6: Please correct “Siogren’s”
To read -- Sjogren’s --

Signed and Sealed this

Fourth Day of December, 2007

JON W. DUDAS
*Director of the United States Patent and Trademark Office*

UNITED STATES PATENT AND TRADEMARK OFFICE

CERTIFICATE OF CORRECTION

PATENT NO. : 7,271,198 B2
APPLICATION NO. : 10/151481
DATED : September 18, 2007
INVENTOR(S) : Kammer et al.

It is certified that error appears in the above-identified patent and that said Letters Patent is hereby corrected as shown below:

In the Specification

Column 1, Lines 14-19: Please delete Statement of Federal Support paragraph and replace with the following:

STATEMENT OF GOVERNMENT SUPPORT
This invention was made with government support under grant number R01 AR039501 awarded by the National Institutes of Health. The government has certain rights in the invention.

Signed and Sealed this
Twenty-third Day of September, 2025

John A. Squires
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1

gaatcctcaa attgcggcac                                              20


<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2

cagaaggtga cttggcatag                                              20


<210> SEQ ID NO 3
<211> LENGTH: 20
<212> TYPE: DNA
<213> ORGANISM: Artificial Sequence
<220> FEATURE:
```

-continued

<223> OTHER INFORMATION: Synthetic oligonucleotide

<400> SEQUENCE: 3
ggtgaaggtc ggagtcaacg 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
caaagttgtc atggatgacc 20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ttgcctggtc ctcctgactg 20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
gatgtctggg tcttggttct 20

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7
atgaaatata caagttatat cttggcttt 29

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
gatgctcttc gacctcgaaa cagcat 26